US010633417B2

(12) United States Patent
McIntosh

(10) Patent No.: US 10,633,417 B2
(45) Date of Patent: Apr. 28, 2020

(54) CONOTOXIN PEPTIDES, PHARMACEUTICAL COMPOSITIONS AND USES THEREOF

(71) Applicant: University of Utah Research Foundation, Salt Lake City, UT (US)

(72) Inventor: J. Michael McIntosh, Salt Lake City, UT (US)

(73) Assignee: UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 481 days.

(21) Appl. No.: 14/894,967

(22) PCT Filed: May 30, 2014

(86) PCT No.: PCT/US2014/040374
§ 371 (c)(1),
(2) Date: Nov. 30, 2015

(87) PCT Pub. No.: WO2014/194284
PCT Pub. Date: Dec. 4, 2014

(65) Prior Publication Data
US 2016/0122388 A1 May 5, 2016

Related U.S. Application Data

(60) Provisional application No. 61/843,135, filed on Jul. 5, 2013, provisional application No. 61/829,633, filed on May 31, 2013.

(51) Int. Cl.

| | |
|---|---|
| *C07K 7/08* | (2006.01) |
| *A61K 38/00* | (2006.01) |
| *C07K 14/435* | (2006.01) |

(52) U.S. Cl.
CPC .......... *C07K 7/08* (2013.01); *C07K 14/43504* (2013.01); *A61K 38/00* (2013.01)

(58) Field of Classification Search
CPC ................................. C07K 7/08; A61K 38/00
See application file for complete search history.

(56) References Cited

U.S. PATENT DOCUMENTS 5,432,155 A * 7/1995 Olivera ................ C07K 14/435 514/12.1
5,514,774 A * 5/1996 Olivera ................ C07K 14/435 530/324
5,595,972 A * 1/1997 Olivera .................. A61K 38/17 435/7.23
5,700,778 A * 12/1997 Olivera ................ C07K 14/435 530/324
5,866,682 A * 2/1999 McIntosh ................. C07K 7/08 530/300
6,265,541 B1 * 7/2001 Olivera .................. A61K 38/08 530/300
6,268,473 B1 * 7/2001 Olivera ........... C07K 14/43504 435/320.1
6,630,573 B1 * 10/2003 Walker ............ C07K 14/43504 530/326
6,727,226 B2 * 4/2004 Olivera ........... C07K 14/43504 514/12.1
6,762,165 B2 * 7/2004 Olivera ........... C07K 14/43504 514/16.4
6,767,895 B2 * 7/2004 Walker ............ C07K 14/43504 514/21.3
6,767,896 B1 * 7/2004 McIntosh ......... C07K 14/43504 514/18.3
6,797,808 B1 * 9/2004 Watkins ........... C07K 14/43504 530/324
6,958,323 B2 * 10/2005 Olivera .................. A61K 38/08 514/15.4
7,279,549 B2 * 10/2007 Watkins ........... C07K 14/43504 530/324
7,387,997 B2 * 6/2008 McIntosh ..................... 514/18.1
7,390,785 B2 * 6/2008 Walker ............ C07K 14/43504 514/18.3
7,666,840 B2 * 2/2010 Watkins ........... C07K 14/43504 514/1.1
7,902,153 B2 * 3/2011 Watkins ........... C07K 14/43504 514/17.7
8,101,573 B2 * 1/2012 McIntosh ......... C07K 14/43504 435/71.3
8,110,549 B2 * 2/2012 Watkins ........... C07K 14/43504 435/71.3

(Continued)

FOREIGN PATENT DOCUMENTS

| | | | |
|---|---|---|---|
| CN | 101448516 | A | 6/2009 |
| WO | WO2002064740 | A2 | 8/2002 |
| WO | 2008/011006 | A2 | 1/2008 |

OTHER PUBLICATIONS

Abdrakhmanova, et al., "In Vitro and In Vivo Characterization of a Novel Negative Allosteric Modulator of Neuronal nAChRs", Neuropharm., vol. 59, 2010, pp. 511-517.

Arredondo, et al., "Central Role of a7 Nicotinic Receptor in Differentiation of the Stratified Squamous Epithelium", J. Cell Biol., vol. 159, 2002, pp. 325-336.

Authier, et al., "Animal Models of Chemotherapy-Evoked Painful Peripheral Neuropathies", Neurotherapeutics, vol. 6, 2009, pp. 620-629.

Azam, et al., "Molecular Basis for the Differential Sensitivity of Rat and Human a9a10 nAChRs to a-Conotoxin RgIA", J. Neurochem., vol. 122, 2012, pp. 1137-1144.

Barreto-Chang, et al., "Calcium Imaging of Cortical Neurons Using Fura-2 AM", J. Vis. Exp., vol. 23, 2009, p. 1-3.

(Continued)

*Primary Examiner* — Amber D Steele
(74) *Attorney, Agent, or Firm* — Michael Best & Friedrich LLP

(57) ABSTRACT

The present disclosure describes analog conotoxin peptides of the α-contoxin peptide RgIA. These analog conotoxin peptides block the α9α10 subtype of the nicotinic acetylcholine receptor (nAChR) and can be used for treating pain, inflammatory conditions, inflammation, and/or cancer.

19 Claims, 8 Drawing Sheets

Specification includes a Sequence Listing.

(56) References Cited

U.S. PATENT DOCUMENTS

Figure 1A:
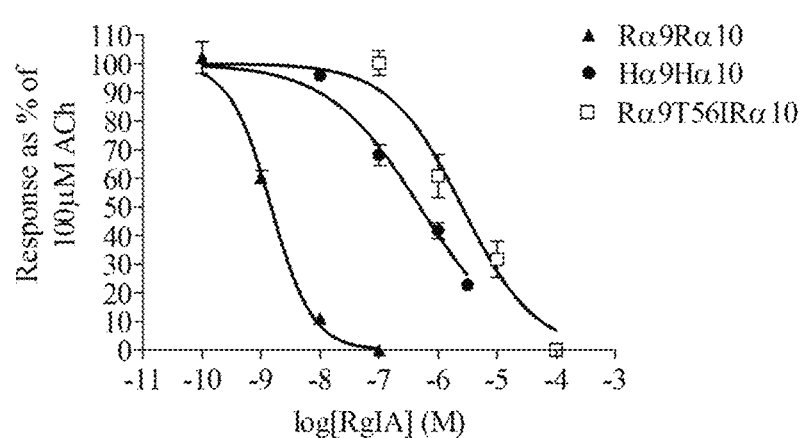

| | | | | |
|---|---|---|---|---|
| 8,487,075 | B2* | 7/2013 | Watkins | C07K 14/43504 530/322 |
| 8,735,541 | B2* | 5/2014 | Watkins | C07K 14/43504 530/326 |
| 9,284,358 | B2* | 3/2016 | McIntosh | C07K 14/43504 |
| 9,469,674 | B2* | 10/2016 | Luo | C07K 14/43504 |
| 9,717,775 | B2* | 8/2017 | McIntosh | A61K 38/1767 |
| 2012/0220539 | A1* | 8/2012 | McIntosh | C07K 14/43504 514/19.4 |
| 2012/0329717 | A1 | 12/2012 | Lewis et al. | |

OTHER PUBLICATIONS

Bennett, et al., "A Peripheral Mononeuropathy in Rat that Produces Disorders of Pain Sensation Like Those Seen in Man", Pain, vol. 33, 1988, pp. 87-107.

Bennett, et al., "Fusion of Green Fluorescent Protein with the Zeocin(TM)-Resistance Marker Allows Visual Screening and Drug Selection of Transfected Eukaryotic Cells", Biotechniques, vol. 24, 1998, pp. 478-482.

Capelli, et al., "Stable Expression and Functional Characterization of a Human Nicotinic Acetylcholine Receptor with a6b2 Properties: Discovery of Selective Antagonists", Br. J. Pharmacol., vol. 163, 2011, pp. 313-329.

Chaplan, et al., "Quantitative Assessment of Tactile Allodynia in the Rat Paw", J. Neurosci. Methods, vol. 53, 1994, pp. 55-63.

Craik, et al., "The Cystine Knot Motif in Toxins and Implications for Drug Design", Toxicon, vol. 39, 2001, pp. 43-60.

Di Cesare Mannelli, et al., "Oxaliplatin-Induced Neuropathy: Oxidative Stress as Pathological Mechanism. Protective Effect of Silibinin", J. Pain, vol. 13, 2012, pp. 276-284.

Elgoyhen, et al., "a10: A Determinant of Nicotinic Cholinergic Receptor Function in Mammalian Vestibular and Cochlear Mechanosensory Hair Cells", Proc. Natl. Acad. Sci. USA, vol. 98, 2001, pp. 3501-3506.

Elgoyhen, et al., "a9: An Acetylcholine Receptor with Novel Pharmacological Properties Expressed in Rat Cochlear Hair Cells", Cell, vol. 79, 1994, pp. 705-715.

Ellison, et al., "a-RgIA: A Novel Conotoxin That Specifically and Potently Blocks the a9a10 nAChR", Biochemistry, vol. 45, 2006, pp. 1511-1517.

Ettinger, et al., "Intrathecal Methotrexate Overdose without Neurotoxicity", Cancer, vol. 41, 1978, pp. 1270-1273.

Gerzanich, et al., "Homomers of a8 and a7 Subunits of Nicotinic Receptors Exhibit Similar Channel but Contrasting Binding Site Properties", Mol. Pharmacol., vol. 45, 1994, pp. 212-220.

Gotti, et al., "Neuronal Nicotinic Receptors: From Structure to Pathology", Prog. Neurobiol., vol. 74, 2004, pp. 363-396.

Hargreaves, et al., "A New and Sensitive Method for Measuring Thermal Nociception in Cutaneous Hyperalgesia", Pain, vol. 32, 1988, pp. 77-88.

Horiki, et al., "Synthesis of the Merrifield Resin Esters of N-Protected Amino Acids with the Aid of Hydrogen Bonding", Chem. Letters, vol. 7, 1978, pp. 165-168.

Kaiser, et al., "Color Test for Detection of Free Terminal Amino Groups in the Solid-Phase Synthesis of Peptides", Anal. Biochem., vol. 34, 1970, pp. 595-598.

Kapoor, "Recent Trends in the Synthesis of Linear Peptides", J. Pharm. Sci., vol. 59, 1970, pp. 1-27.

Kracun, et al., "Influence of the M3-M4 Intracellular Domain upon Nicotinic Acetylcholine Receptor Assembly, Targeting and Function", Br. J. Pharmacol., vol. 153, 2008, pp. 1474-1484.

Karlin, "Emerging Structure of the Nicotinic Acetylcholine Receptors", Nat. Rev. Neurosci., vol. 3, 2002, pp. 102-114.

Kim, et al., "An Experimental Model for Peripheral Neuropathy Produced by Segmental Spinal Nerve Ligation in the Rat", Pain, vol. 50, 1992, pp. 355-363.

Kurzen, et al., "Phenotypical and Molecular Profiling of the Extraneuronal Cholinergic System of the Skin", J. Invest. Dermatol., vol. 123, 2004, pp. 937-949.

Le Novere, et al., "The Diversity of Subunit Composition in nAChRs: Evolutionary Origins, Physiologic and Pharmacologic Consequences", J. Neurobiol., vol. 53, 2002, pp. 447-456.

Lee, et al., "Overexpression and Activation of the a9-Nicotinic Receptor during Tumorigenesis in Human Breast Epithelial Cells", J. Natl. Cancer Inst., vol. 102, 2010, pp. 1322-1335.

Lewis, "Conotoxins as Selective Inhibitors of Neuronal Ion Channels, Receptors and Transporters", IUBMB Life, vol. 56, 2004, pp. 89-93.

Linnoila, "From Nicotine to Breast Cancer, Implications of Cholinergic Receptor Pathway", J. Natl. Cancer Inst., vol. 102, 2010, pp. 1298-1299.

Lips, et al., "Coexpression of a9 and a10 Nicotinic Acetylcholine Receptors in Rat Dorsal Root Ganglion Neurons", Neuroscience, vol. 115, 2002, pp. 1-5.

Livett, et al., "Drugs from the Sea: Conopeptides as Potential Therapeutics", Curr. Med. Chem., vol. 11, 2004, pp. 1715-1723.

Luer, et al., "Vancomycin Administration into the Cerebrospinal Fluid: A Review", Ann. Pharmcother., vol. 27, 1993, pp. 912-921.

McIntosh, et al., "A Novel a-Conotoxin, Pela, Cloned from Conus pergrandis, Discriminates between Rat a9a10 and a7 Nicotinic Cholinergic Receptors", J. Biol. Chem., vol. 280, 2005, pp. 30107-30112.

McIntosh, et al., "Conus Peptides Targeted to Specific Nicotinic Acetylcholine Receptor Subtypes", Annu. Rev. Biochem., vol. 68, 1999, pp. 59-88.

Nguyen, et al., "Novel Human a9 Acetylcholine Receptor Regulating Keratinocyte Adhesion is Targeted by Pemphigus Vulgaris Autoimmunity", Am. J. Pathol., vol. 157, 2000, pp. 1377-1391.

Peng, et al., "Characterization of the Human Nicotinic Acetylcholine Receptor Subunit Alpha (a) 9 (CHRNA9) and Alpha (a) 10 (CHRNA10) in Lymphocytes", Life Sci., vol. 76, 2004, pp. 263-280.

Pitcher, et al., "Paw Withdrawal Threshold in the Von Frey Hair Test is Influenced by the Surface on which the Rat Stands", J. Neurosci. Methods, vol. 87, 1999, pp. 185-193.

Rivier, et al., "Solid-Phase Synthesis of Somatostatin and Glucagon-Selective Analogs in Gram Quantities", Biopolymers, vol. 17, 1978, pp. 1927-1938.

Sgard, et al., "A Novel Human Nicotinic Receptor Subunit, a10, That Confers Functionality to the a9-Subunit", Mol. Pharmacol., vol. 61, 2002, pp. 150-159.

Search Report and Written Opinion dated Oct. 22, 2015 in International Application No. PCT/US14/40374.

Teichert, et al., "Functional Profiling of Neurons through Cellular Neuropharmacology", Proc. Natl. Acad. Sci. USA, vol. 109, 2012, pp. 1388-1395.

Terlau, et al., "Conus Venoms: A Rich Source of Novel Ion Channel-Targeted Peptides", Physiol. Rev., vol. 84, 2004, pp. 41-68.

Vincler, et al., "Molecular Mechanism for Analgesia Involving Specific Antagonism of a9a10 Nicotinic Acetylcholine Receptors", Proc. Natl. Acad. Sci. USA, vol. 103, 2006, pp. 17880-17884.

Wang, et al., "Conus Peptides—A Rich Pharmaceutical Treasure", Acta Biochim. Biophys. Sin., vol. 36, 2004, pp. 713-723.

Xiao, et al., "Chronic Nicotine Selectively Enhances a4b2* Nicotinic Acetylcholine Receptors in the Nigrostriatal Dopamine Pathway", J. Neurosci., vol. 29, 2009, pp. 12428-12439.

Xiao, et al., "Rat a3/b4 Subtype of Neuronal Nicotinic Acetylcholine Receptor Stably Expressed in a Transfected Cell Line: Pharmacology of Ligand Binding and Function", Mol. Pharmacol., vol. 54, 1998, pp. 322-333.

Zimm, et al., "Cerebrospinal Fluid Pharmacokinetics of Intraventricular and Intravenous Aziridinylbenzoquinone", Cancer Res., vol. 44, 1984, pp. 1698-1701.

Azam et al., "Molecular Interaction of α-Conotoxin RgIA with the Rat α9α10 Nicotinic Acetylcholine Receptor," Molecular Pharmacology, 2015, 87(5):855-864.

Craig et al., "Post-translationally modified neuropeptides from Conus venoms," European Journal of Biochemistry, 1999, 264(2)271-275.

(56) References Cited

OTHER PUBLICATIONS

Ellison et al., "α-RgIA, a Novel Conotoxin that Blocks the α9α10 nAChR: Structure and Identification of Key Receptor Binding Residues," Journal of Molecular Biology, 2008, 377(4):1216-1227.
Mohammadi et al., "Conotoxin Interactions with α9α10-nAChRs: Is the α9α10-Nicotinic Acetylcholine Receptor an Important Therapeutic Target for Pain Management?" Toxins, 2015, 7(10):3916-3932.
Muttenthaler et al., "Solving the α-Conotoxin Folding Problem: Efficient Selenium-Directed On-Resin Generation of More Potent and Stable Nicotinic Acetylcholine Receptor Antagonists," Journal of the American Chemical Society, 2010, 132(10):3514-3522.
Raffa et al., "Diselenium, instead of disulfide, bonded analogs of conotoxins: novel synthesis and pharmacotherapeutic potential," Life Sciences, 2010, 87(15-16):451-456.
Walewska et al., "Expanding chemical diversity of conotoxins: peptoid-peptide chimeras of the sodium channel blocker u-KIIIA and its selenopeptide analogues," European Journal of Medicinal Chemistry, 2013, 65:144-150.
Israeli Patent Office Action for Application No. 242854 dated Sep. 25, 2019 (5 pages, English translation included).
Australian Patent Office Examination Report No. 1 for Application No. 2014273883 dated Oct. 25, 2018 (8 pages).
Chinese Patent Office Action for Application No. 201480037106.7 dated Jul. 4, 2018 (7 pages, Statement of relevance included).
Chinese Patent Office Action for Application No. 201480037106.7 dated May 27, 2019 (3 pages, English translation only).
European Patent Office Action for Application No. 14803447.0 dated Aug. 6, 2018 (6 pages).
European Patent Office Extended Search Report for Application No. 14803477.0 dated Nov. 25, 2016 (11 pages).
Taiwan Patent Office Action for Application No. 103119136 dated Jun. 19, 2019 (16 pages, English translation included).
Taiwan Patent Office Action for Application No. 103119136 dated Dec. 12, 2018 (9 pages, English translation included).

\* cited by examiner

SEQUENCE LISTING

```
<160> NUMBER OF SEQ ID NOS: 37

<210> SEQ ID NO 1
<211> LENGTH: 13
<212> TYPE: PRT
<213> ORGANISM: Conus regius

<400> SEQUENCE: 1

Gly Cys Cys Ser Asp Pro Arg Cys Arg Tyr Arg Cys Arg
1               5                   10

<210> SEQ ID NO 2
<211> LENGTH: 13
<212> TYPE: PRT
```

```
<213> ORGANISM: Artificial Sequence
<220> FEATURE:
<223> OTHER INFORMATION: Synthetic
<220> FEATURE:
<221> NAME/KEY: VARIANT
<222> LOCATION: (9)..(9)
<223> OTHER INFORMATION: Xaa at position 9 is Arg or citrulline
<220> FEATURE:
<221> NAME/KEY: MISC_FEATURE
<222> LOCATION: (10)..(10)
<223> OTHER INFORMATION: Xaa at position 10 is mono-iodo-Tyr
<220> FEATURE:
<221> NAME/KEY: VARIANT
<222> LOCATION: (13)..(13)
<223> OTHER INFORMATION: Xaa at position 13 is Tyr

<400> SEQUENCE: 2

Gly Cys Cys Thr Asp Pro Arg Cys Xaa Xaa Gln Cys Xaa
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (9)..(9)
<223> OTHER INFORMATION: Xaa at position 9 is citrulline
<220> FEATURE:
<221> NAME/KEY: MISC_FEATURE
<222> LOCATION: (10)..(10)
<223> OTHER INFORMATION: Xaa at position 10 is mono-iodo-Tyr

<400> SEQUENCE: 3

Gly Cys Cys Thr Asp Pro Arg Cys Xaa Xaa Gln Cys Tyr
1               5                   10

<210> SEQ ID NO 4
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (9)..(9)
<223> OTHER INFORMATION: Xaa at position 9 is citrulline
<220> FEATURE:
<221> NAME/KEY: MISC_FEATURE
<222> LOCATION: (10)..(10)
<223> OTHER INFORMATION: Xaa at position 10 is mono-iodo-Tyr

<400> SEQUENCE: 4

Gly Cys Cys Thr Asp Pro Arg Cys Xaa Xaa Gln Cys Arg Arg Arg
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (9)..(9)
<223> OTHER INFORMATION: Xaa at position 9 is citrulline
<220> FEATURE:
<221> NAME/KEY: MISC_FEATURE
<222> LOCATION: (10)..(10)
<223> OTHER INFORMATION: Xaa at position 10 is mono-iodo-Tyr
```

-continued

```
<400> SEQUENCE: 5

Gly Cys Cys Thr Asp Pro Arg Cys Xaa Xaa Gln Cys Tyr Arg Arg
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (9)..(9)
<223> OTHER INFORMATION: Xaa at position 9 is citrulline
<220> FEATURE:
<221> NAME/KEY: MISC_FEATURE
<222> LOCATION: (10)..(10)
<223> OTHER INFORMATION: Xaa at position 10 is mono-iodo-Tyr

<400> SEQUENCE: 6

Gly Cys Cys Thr Asp Pro Arg Cys Xaa Xaa Gln Cys Arg Arg Tyr
1               5                   10                  15

<210> SEQ ID NO 7
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (9)..(9)
<223> OTHER INFORMATION: Xaa at position 9 is citrulline
<220> FEATURE:
<221> NAME/KEY: MISC_FEATURE
<222> LOCATION: (10)..(10)
<223> OTHER INFORMATION: Xaa at position 10 is mono-iodo-Tyr

<400> SEQUENCE: 7

Gly Cys Cys Thr Asp Pro Arg Cys Xaa Xaa Gln Cys Phe
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (9)..(9)
<223> OTHER INFORMATION: Xaa at position 9 is citrulline
<220> FEATURE:
<221> NAME/KEY: MISC_FEATURE
<222> LOCATION: (10)..(10)
<223> OTHER INFORMATION: Xaa at position 10 is mono-iodo-Tyr

<400> SEQUENCE: 8

Gly Cys Cys Thr Asp Pro Arg Cys Xaa Xaa Gln Cys Trp
1               5                   10

<210> SEQ ID NO 9
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (9)..(9)
<223> OTHER INFORMATION: Xaa at position 9 is citrulline
```

```
<220> FEATURE:
<221> NAME/KEY: MISC_FEATURE
<222> LOCATION: (10)..(10)
<223> OTHER INFORMATION: Xaa at position 10 is mono-iodo-Tyr

<400> SEQUENCE: 9

Gly Cys Cys Thr Asp Pro Arg Cys Xaa Xaa Gln Cys Tyr Tyr
1               5                   10

<210> SEQ ID NO 10
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (9)..(9)
<223> OTHER INFORMATION: Xaa at position 9 is citrulline
<220> FEATURE:
<221> NAME/KEY: MISC_FEATURE
<222> LOCATION: (10)..(10)
<223> OTHER INFORMATION: Xaa at position 10 is mono-iodo-Tyr

<400> SEQUENCE: 10

Gly Cys Cys Thr Asp Pro Arg Cys Xaa Xaa Gln Cys Tyr Arg
1               5                   10

<210> SEQ ID NO 11
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (10)..(10)
<223> OTHER INFORMATION: Xaa at position 10 is mono-iodo-Tyr

<400> SEQUENCE: 11

Gly Cys Cys Thr Asp Pro Arg Cys Arg Xaa Gln Cys Tyr
1               5                   10

<210> SEQ ID NO 12
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (10)..(10)
<223> OTHER INFORMATION: Xaa at position 10 is mono-iodo-Tyr

<400> SEQUENCE: 12

Gly Cys Cys Thr Asp Pro Arg Cys Arg Xaa Gln Cys Arg Arg Arg
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (10)..(10)
<223> OTHER INFORMATION: Xaa at position 10 is mono-iodo-Tyr

<400> SEQUENCE: 13
```

Gly Cys Cys Thr Asp Pro Arg Cys Arg Xaa Gln Cys Tyr Arg Arg
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (10)..(10)
<223> OTHER INFORMATION: Xaa at position 10 is mono-iodo-Tyr

<400> SEQUENCE: 14

Gly Cys Cys Thr Asp Pro Arg Cys Arg Xaa Gln Cys Arg Arg Tyr
1               5                   10                  15

<210> SEQ ID NO 15
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (10)..(10)
<223> OTHER INFORMATION: Xaa at position 10 is mono-iodo-Tyr

<400> SEQUENCE: 15

Gly Cys Cys Thr Asp Pro Arg Cys Arg Xaa Gln Cys Phe
1               5                   10

<210> SEQ ID NO 16
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (10)..(10)
<223> OTHER INFORMATION: Xaa at position 10 is mono-iodo-Tyr

<400> SEQUENCE: 16

Gly Cys Cys Thr Asp Pro Arg Cys Arg Xaa Gln Cys Trp
1               5                   10

<210> SEQ ID NO 17
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (10)..(10)
<223> OTHER INFORMATION: Xaa at position 10 is mono-iodo-Tyr

<400> SEQUENCE: 17

Gly Cys Cys Thr Asp Pro Arg Cys Arg Xaa Gln Cys Tyr Tyr
1               5                   10

<210> SEQ ID NO 18
<211> LENGTH: 14
<212> TYPE: PRT
<213> ORGANISM: Artificial Sequence
<220> FEATURE:
<223> OTHER INFORMATION: Synthetic
<220> FEATURE:

```
<221> NAME/KEY: MISC_FEATURE
<222> LOCATION: (10)..(10)
<223> OTHER INFORMATION: Xaa at position 10 is mono-iodo-Tyr

<400> SEQUENCE: 18

Gly Cys Cys Thr Asp Pro Arg Cys Arg Xaa Gln Cys Tyr Arg
1               5                   10

<210> SEQ ID NO 19
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (9)..(9)
<223> OTHER INFORMATION: Xaa at position 9 is citrulline
<220> FEATURE:
<221> NAME/KEY: MISC_FEATURE
<222> LOCATION: (10)..(10)
<223> OTHER INFORMATION: Xaa at position 10 is mono-iodo-Tyr

<400> SEQUENCE: 19

Gly Cys Cys Thr Asp Pro Arg Cys Xaa Xaa Gln Cys Arg
1               5                   10

<210> SEQ ID NO 20
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa at position 2 is selenocysteine
<220> FEATURE:
<221> NAME/KEY: MISC_FEATURE
<222> LOCATION: (3)..(3)
<223> OTHER INFORMATION: Xaa at position 3 is selenocysteine
<220> FEATURE:
<221> NAME/KEY: MISC_FEATURE
<222> LOCATION: (9)..(9)
<223> OTHER INFORMATION: Xaa at position 9 is citrulline
<220> FEATURE:
<221> NAME/KEY: MISC_FEATURE
<222> LOCATION: (10)..(10)
<223> OTHER INFORMATION: Xaa at position 10 is mono-iodo-Tyr

<400> SEQUENCE: 20

Gly Xaa Xaa Thr Asp Pro Arg Cys Xaa Xaa Gln Cys Arg
1               5                   10

<210> SEQ ID NO 21
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (10)..(10)
<223> OTHER INFORMATION: Xaa at position 10 is mono-iodo-Tyr

<400> SEQUENCE: 21

Gly Cys Cys Ser Asp Pro Arg Cys Arg Xaa Arg Cys Arg
1               5                   10

<210> SEQ ID NO 22
<211> LENGTH: 13
```

```
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (2)..(2)
<223> OTHER INFORMATION: Xaa at position 2 is Cys or selenocysteine
<220> FEATURE:
<221> NAME/KEY: VARIANT
<222> LOCATION: (3)..(3)
<223> OTHER INFORMATION: Xaa at position 3 is Cys or selenocysteine
<220> FEATURE:
<221> NAME/KEY: VARIANT
<222> LOCATION: (4)..(4)
<223> OTHER INFORMATION: Xaa at position 4 is Ser or Thr
<220> FEATURE:
<221> NAME/KEY: VARIANT
<222> LOCATION: (8)..(8)
<223> OTHER INFORMATION: Xaa at position 8 is Cys or selenocysteine
<220> FEATURE:
<221> NAME/KEY: VARIANT
<222> LOCATION: (9)..(9)
<223> OTHER INFORMATION: Xaa at position 9 is Arg, citrulline, or
     [omega]-nitro-Arg
<220> FEATURE:
<221> NAME/KEY: VARIANT
<222> LOCATION: (10)..(10)
<223> OTHER INFORMATION: Xaa at position 10 is Tyr or  mono-iodo-Tyr
<220> FEATURE:
<221> NAME/KEY: VARIANT
<222> LOCATION: (11)..(11)
<223> OTHER INFORMATION: Xaa at position 11 is Arg, Gln, or Glu
<220> FEATURE:
<221> NAME/KEY: VARIANT
<222> LOCATION: (12)..(12)
<223> OTHER INFORMATION: Xaa at position 12 is Cys or selenocysteine
<220> FEATURE:
<221> NAME/KEY: VARIANT
<222> LOCATION: (13)..(13)
<223> OTHER INFORMATION: Xaa at position 13 is Arg

<400> SEQUENCE: 22

Gly Xaa Xaa Xaa Asp Pro Arg Xaa Xaa Xaa Xaa Xaa Xaa
1               5                   10

<210> SEQ ID NO 23
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (9)..(9)
<223> OTHER INFORMATION: Xaa at position 9 is Arg or citrulline
<220> FEATURE:
<221> NAME/KEY: MISC_FEATURE
<222> LOCATION: (10)..(10)
<223> OTHER INFORMATION: Xaa at position 10 is mono-iodo-Tyr
<220> FEATURE:
<221> NAME/KEY: VARIANT
<222> LOCATION: (13)..(13)
<223> OTHER INFORMATION: Xaa at position 13 is Phe

<400> SEQUENCE: 23

Gly Cys Cys Thr Asp Pro Arg Cys Xaa Xaa Gln Cys Xaa
1               5                   10

<210> SEQ ID NO 24
<211> LENGTH: 13
<212> TYPE: PRT
<213> ORGANISM: Artificial Sequence
<220> FEATURE:
<223> OTHER INFORMATION: Synthetic
```

```
<220> FEATURE:
<221> NAME/KEY: VARIANT
<222> LOCATION: (9)..(9)
<223> OTHER INFORMATION: Xaa at position 9 is Arg or citrulline
<220> FEATURE:
<221> NAME/KEY: MISC_FEATURE
<222> LOCATION: (10)..(10)
<223> OTHER INFORMATION: Xaa at position 10 is mono-iodo-Tyr
<220> FEATURE:
<221> NAME/KEY: VARIANT
<222> LOCATION: (13)..(13)
<223> OTHER INFORMATION: Xaa at position 13 is Trp

<400> SEQUENCE: 24

Gly Cys Cys Thr Asp Pro Arg Cys Xaa Xaa Gln Cys Xaa
1               5                   10

<210> SEQ ID NO 25
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (9)..(9)
<223> OTHER INFORMATION: Xaa at position 9 Arg or citrulline
<220> FEATURE:
<221> NAME/KEY: MISC_FEATURE
<222> LOCATION: (10)..(10)
<223> OTHER INFORMATION: Xaa at position 10 is mono-iodo-Tyr
<220> FEATURE:
<221> NAME/KEY: VARIANT
<222> LOCATION: (13)..(13)
<223> OTHER INFORMATION: Xaa at position 13 is Tyr
<220> FEATURE:
<221> NAME/KEY: VARIANT
<222> LOCATION: (14)..(14)
<223> OTHER INFORMATION: Xaa at position 14 is Tyr

<400> SEQUENCE: 25

Gly Cys Cys Thr Asp Pro Arg Cys Xaa Xaa Gln Cys Xaa Xaa
1               5                   10

<210> SEQ ID NO 26
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (9)..(9)
<223> OTHER INFORMATION: Xaa at position 9 is Arg or citrulline
<220> FEATURE:
<221> NAME/KEY: MISC_FEATURE
<222> LOCATION: (10)..(10)
<223> OTHER INFORMATION: Xaa at position 10 is mono-iodo-Tyr
<220> FEATURE:
<221> NAME/KEY: VARIANT
<222> LOCATION: (13)..(13)
<223> OTHER INFORMATION: Xaa at position 13 is Tyr
<220> FEATURE:
<221> NAME/KEY: VARIANT
<222> LOCATION: (14)..(14)
<223> OTHER INFORMATION: Xaa at position 14 is Arg

<400> SEQUENCE: 26

Gly Cys Cys Thr Asp Pro Arg Cys Xaa Xaa Gln Cys Xaa Xaa
1               5                   10

<210> SEQ ID NO 27
<211> LENGTH: 15
```

```
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (9)..(9)
<223> OTHER INFORMATION: Xaa at position 9 is Arg or citrulline
<220> FEATURE:
<221> NAME/KEY: MISC_FEATURE
<222> LOCATION: (10)..(10)
<223> OTHER INFORMATION: Xaa at position 10 is mono-iodo-Tyr
<220> FEATURE:
<221> NAME/KEY: VARIANT
<222> LOCATION: (13)..(13)
<223> OTHER INFORMATION: Xaa at position 13 is Arg
<220> FEATURE:
<221> NAME/KEY: VARIANT
<222> LOCATION: (14)..(14)
<223> OTHER INFORMATION: Xaa at position 14 is Arg
<220> FEATURE:
<221> NAME/KEY: VARIANT
<222> LOCATION: (15)..(15)
<223> OTHER INFORMATION: Xaa at position 15 is Arg

<400> SEQUENCE: 27

Gly Cys Cys Thr Asp Pro Arg Cys Xaa Xaa Gln Cys Xaa Xaa Xaa
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (9)..(9)
<223> OTHER INFORMATION: Xaa at position 9 is Arg or citrulline
<220> FEATURE:
<221> NAME/KEY: MISC_FEATURE
<222> LOCATION: (10)..(10)
<223> OTHER INFORMATION: Xaa at position 10 is mono-iodo-Tyr
<220> FEATURE:
<221> NAME/KEY: VARIANT
<222> LOCATION: (13)..(13)
<223> OTHER INFORMATION: Xaa at position 13 is Arg
<220> FEATURE:
<221> NAME/KEY: VARIANT
<222> LOCATION: (14)..(14)
<223> OTHER INFORMATION: Xaa at position 14 is Arg
<220> FEATURE:
<221> NAME/KEY: VARIANT
<222> LOCATION: (15)..(15)
<223> OTHER INFORMATION: Xaa at position 15 is Tyr

<400> SEQUENCE: 28

Gly Cys Cys Thr Asp Pro Arg Cys Xaa Xaa Gln Cys Xaa Xaa Xaa
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (9)..(9)
<223> OTHER INFORMATION: Xaa at position 9 is Arg or citrulline
<220> FEATURE:
<221> NAME/KEY: MISC_FEATURE
<222> LOCATION: (10)..(10)
<223> OTHER INFORMATION: Xaa at position 10 is mono-iodo-Tyr
<220> FEATURE:
```

```
<221> NAME/KEY: VARIANT
<222> LOCATION: (13)..(13)
<223> OTHER INFORMATION: Xaa at position 13 is Tyr
<220> FEATURE:
<221> NAME/KEY: VARIANT
<222> LOCATION: (14)..(14)
<223> OTHER INFORMATION: Xaa at position 14 is Arg
<220> FEATURE:
<221> NAME/KEY: VARIANT
<222> LOCATION: (15)..(15)
<223> OTHER INFORMATION: Xaa at position 15 is Arg

<400> SEQUENCE: 29

Gly Cys Cys Thr Asp Pro Arg Cys Xaa Xaa Gln Cys Xaa Xaa Xaa
1               5                   10                  15

<210> SEQ ID NO 30
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (2)..(2)
<223> OTHER INFORMATION: Xaa at position 2 is Cys or selenocysteine
<220> FEATURE:
<221> NAME/KEY: VARIANT
<222> LOCATION: (3)..(3)
<223> OTHER INFORMATION: Xaa at position 3 is Cys or selenocysteine
<220> FEATURE:
<221> NAME/KEY: VARIANT
<222> LOCATION: (4)..(4)
<223> OTHER INFORMATION: Xaa at position 4 is Ser or Thr
<220> FEATURE:
<221> NAME/KEY: VARIANT
<222> LOCATION: (8)..(8)
<223> OTHER INFORMATION: Xaa at position 8 is Cys or selenocysteine
<220> FEATURE:
<221> NAME/KEY: VARIANT
<222> LOCATION: (9)..(9)
<223> OTHER INFORMATION: Xaa at position 9 is Arg, citrullline, or
      [omega]-nitro-Arg
<220> FEATURE:
<221> NAME/KEY: VARIANT
<222> LOCATION: (10)..(10)
<223> OTHER INFORMATION: Xaa at position 10 is Tyr or mono-iodo-Tyr
<220> FEATURE:
<221> NAME/KEY: VARIANT
<222> LOCATION: (11)..(11)
<223> OTHER INFORMATION: Xaa at position 11 is Arg, Gln, or Glu
<220> FEATURE:
<221> NAME/KEY: VARIANT
<222> LOCATION: (12)..(12)
<223> OTHER INFORMATION: Xaa at position 12 is Cys or selenocysteine
<220> FEATURE:
<221> NAME/KEY: VARIANT
<222> LOCATION: (13)..(13)
<223> OTHER INFORMATION: Xaa at position 13 is Tyr

<400> SEQUENCE: 30

Gly Xaa Xaa Xaa Asp Pro Arg Xaa Xaa Xaa Xaa Xaa Xaa
1               5                   10

<210> SEQ ID NO 31
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (2)..(2)
<223> OTHER INFORMATION: Xaa at position 2 is Cys or selenocysteine
<220> FEATURE:
```

```
<221> NAME/KEY: VARIANT
<222> LOCATION: (3)..(3)
<223> OTHER INFORMATION: Xaa at position 3 is Cys or selenocysteine
<220> FEATURE:
<221> NAME/KEY: VARIANT
<222> LOCATION: (4)..(4)
<223> OTHER INFORMATION: Xaa at position 4 is Ser of Thr
<220> FEATURE:
<221> NAME/KEY: VARIANT
<222> LOCATION: (4)..(4)
<223> OTHER INFORMATION: Xaa at position 4 is Ser or Thr
<220> FEATURE:
<221> NAME/KEY: VARIANT
<222> LOCATION: (8)..(8)
<223> OTHER INFORMATION: Xaa at position 8 is Cys or selenocysteine
<220> FEATURE:
<221> NAME/KEY: VARIANT
<222> LOCATION: (9)..(9)
<223> OTHER INFORMATION: Xaa at position 9 is Arg, citrulline, or
     [omega]-nitro-Arg
<220> FEATURE:
<221> NAME/KEY: VARIANT
<222> LOCATION: (10)..(10)
<223> OTHER INFORMATION: Xaa at position 10 is Tyr or mono-iodo-Tyr
<220> FEATURE:
<221> NAME/KEY: VARIANT
<222> LOCATION: (11)..(11)
<223> OTHER INFORMATION: Xaa at position 11 is Arg, Gln, or Glu
<220> FEATURE:
<221> NAME/KEY: VARIANT
<222> LOCATION: (12)..(12)
<223> OTHER INFORMATION: Xaa at position 12 is Cys or selenocysteine
<220> FEATURE:
<221> NAME/KEY: VARIANT
<222> LOCATION: (13)..(13)
<223> OTHER INFORMATION: Xaa at position 13 is Phe

<400> SEQUENCE: 31

Gly Xaa Xaa Xaa Asp Pro Arg Xaa Xaa Xaa Xaa Xaa
1               5                   10

<210> SEQ ID NO 32
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (2)..(2)
<223> OTHER INFORMATION: Xaa at position 2 is Cys or selenocysteine
<220> FEATURE:
<221> NAME/KEY: VARIANT
<222> LOCATION: (3)..(3)
<223> OTHER INFORMATION: Xaa at position 3 is Cys or selenocysteine
<220> FEATURE:
<221> NAME/KEY: VARIANT
<222> LOCATION: (4)..(4)
<223> OTHER INFORMATION: Xaa at position 4 is Ser or Thr
<220> FEATURE:
<221> NAME/KEY: VARIANT
<222> LOCATION: (8)..(8)
<223> OTHER INFORMATION: Xaa at position 8 is Cys or selenocysteine
<220> FEATURE:
<221> NAME/KEY: VARIANT
<222> LOCATION: (9)..(9)
<223> OTHER INFORMATION: Xaa at position 9 Arg, citrulline, or
     [omega]-nitro-Arg
<220> FEATURE:
<221> NAME/KEY: VARIANT
<222> LOCATION: (10)..(10)
<223> OTHER INFORMATION: Xaa at position 10 is Tyr or mono-iodo-Tyr
<220> FEATURE:
<221> NAME/KEY: VARIANT
<222> LOCATION: (11)..(11)
<223> OTHER INFORMATION: Xaa at position 11 is Arg, Gln, or Glu
<220> FEATURE:
```

```
<221> NAME/KEY: VARIANT
<222> LOCATION: (12)..(12)
<223> OTHER INFORMATION: Xaa at position 12 is Cys or selenocysteine
<220> FEATURE:
<221> NAME/KEY: VARIANT
<222> LOCATION: (13)..(13)
<223> OTHER INFORMATION: Xaa at position 13 is Trp

<400> SEQUENCE: 32

Gly Xaa Xaa Xaa Asp Pro Arg Xaa Xaa Xaa Xaa Xaa Xaa
1               5                   10

<210> SEQ ID NO 33
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (2)..(2)
<223> OTHER INFORMATION: Xaa at position 2 is Cys or selenocysteine
<220> FEATURE:
<221> NAME/KEY: VARIANT
<222> LOCATION: (3)..(3)
<223> OTHER INFORMATION: Xaa at position 3 is Cys or selenocysteine
<220> FEATURE:
<221> NAME/KEY: VARIANT
<222> LOCATION: (4)..(4)
<223> OTHER INFORMATION: Xaa at position 4 is Ser or Thr
<220> FEATURE:
<221> NAME/KEY: VARIANT
<222> LOCATION: (8)..(8)
<223> OTHER INFORMATION: Xaa at position 8 is Cys or selenocysteine
<220> FEATURE:
<221> NAME/KEY: VARIANT
<222> LOCATION: (9)..(9)
<223> OTHER INFORMATION: Xaa at position 9 is Arg, citrulline, or
      [omega]-nitro-Arg
<220> FEATURE:
<221> NAME/KEY: VARIANT
<222> LOCATION: (10)..(10)
<223> OTHER INFORMATION: Xaa at position 10 is Tyr or mono-iodo-Tyr
<220> FEATURE:
<221> NAME/KEY: VARIANT
<222> LOCATION: (11)..(11)
<223> OTHER INFORMATION: Xaa at position 11 is Arg, Gln, or Glu
<220> FEATURE:
<221> NAME/KEY: VARIANT
<222> LOCATION: (12)..(12)
<223> OTHER INFORMATION: Xaa at position 12 is Cys or selenocysteine
<220> FEATURE:
<221> NAME/KEY: VARIANT
<222> LOCATION: (13)..(13)
<223> OTHER INFORMATION: Xaa at position 13 is Tyr
<220> FEATURE:
<221> NAME/KEY: VARIANT
<222> LOCATION: (14)..(14)
<223> OTHER INFORMATION: Xaa at position 14 is Tyr

<400> SEQUENCE: 33

Gly Xaa Xaa Xaa Asp Pro Arg Xaa Xaa Xaa Xaa Xaa Xaa
1               5                   10

<210> SEQ ID NO 34
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (2)..(2)
<223> OTHER INFORMATION: Xaa at position 2 is Cys or selenocysteine
<220> FEATURE:
```

```
<221> NAME/KEY: VARIANT
<222> LOCATION: (3)..(3)
<223> OTHER INFORMATION: Xaa at position 3 is Cys or selenocysteine
<220> FEATURE:
<221> NAME/KEY: VARIANT
<222> LOCATION: (4)..(4)
<223> OTHER INFORMATION: Xaa at position 4 is Ser or Thr
<220> FEATURE:
<221> NAME/KEY: VARIANT
<222> LOCATION: (8)..(8)
<223> OTHER INFORMATION: Xaa at position 8 is Cys or selenocysteine
<220> FEATURE:
<221> NAME/KEY: VARIANT
<222> LOCATION: (9)..(9)
<223> OTHER INFORMATION: Xaa at position 9 is Arg, citrulline, or
      [omega]-nitro-Arg
<220> FEATURE:
<221> NAME/KEY: VARIANT
<222> LOCATION: (10)..(10)
<223> OTHER INFORMATION: Xaa at position 10 is Tyr or  mono-iodo-Tyr
<220> FEATURE:
<221> NAME/KEY: VARIANT
<222> LOCATION: (11)..(11)
<223> OTHER INFORMATION: Xaa at position 11 is Arg, Gln, or Glu
<220> FEATURE:
<221> NAME/KEY: VARIANT
<222> LOCATION: (12)..(12)
<223> OTHER INFORMATION: Xaa at position 12 is Cys or selenocysteine
<220> FEATURE:
<221> NAME/KEY: VARIANT
<222> LOCATION: (13)..(13)
<223> OTHER INFORMATION: Xaa at position 13 is Tyr
<220> FEATURE:
<221> NAME/KEY: VARIANT
<222> LOCATION: (14)..(14)
<223> OTHER INFORMATION: Xaa at position 14 is Arg

<400> SEQUENCE: 34

Gly Xaa Xaa Xaa Asp Pro Arg Xaa Xaa Xaa Xaa Xaa Xaa Xaa
1               5                   10

<210> SEQ ID NO 35
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (2)..(2)
<223> OTHER INFORMATION: Xaa at position 2 is Cys or selenocysteine
<220> FEATURE:
<221> NAME/KEY: VARIANT
<222> LOCATION: (3)..(3)
<223> OTHER INFORMATION: Xaa at position 3 is Cys or selenocysteine
<220> FEATURE:
<221> NAME/KEY: VARIANT
<222> LOCATION: (4)..(4)
<223> OTHER INFORMATION: Xaa at position 4 is Ser or Thr
<220> FEATURE:
<221> NAME/KEY: VARIANT
<222> LOCATION: (8)..(8)
<223> OTHER INFORMATION: Xaa at position 8 is Cys or selenocysteine
<220> FEATURE:
<221> NAME/KEY: VARIANT
<222> LOCATION: (9)..(9)
<223> OTHER INFORMATION: Xaa at position 9 is Arg, citrulline, or
      [omega]-nitro-Arg
<220> FEATURE:
<221> NAME/KEY: VARIANT
<222> LOCATION: (10)..(10)
<223> OTHER INFORMATION: Xaa at position 10 is Tyr or mono-iodo-Tyr
<220> FEATURE:
<221> NAME/KEY: VARIANT
<222> LOCATION: (11)..(11)
<223> OTHER INFORMATION: Xaa at position 11 is Arg, Gln, or Glu
<220> FEATURE:
```

```
<221> NAME/KEY: VARIANT
<222> LOCATION: (12)..(12)
<223> OTHER INFORMATION: Xaa at position 12 is Cys or selenocysteine
<220> FEATURE:
<221> NAME/KEY: VARIANT
<222> LOCATION: (13)..(13)
<223> OTHER INFORMATION: Xaa at position 13 is Arg
<220> FEATURE:
<221> NAME/KEY: VARIANT
<222> LOCATION: (14)..(14)
<223> OTHER INFORMATION: Xaa at position 14 is Arg
<220> FEATURE:
<221> NAME/KEY: VARIANT
<222> LOCATION: (15)..(15)
<223> OTHER INFORMATION: Xaa at position 15 is Arg

<400> SEQUENCE: 35

Gly Xaa Xaa Xaa Asp Pro Arg Xaa Xaa Xaa Xaa Xaa Xaa Xaa
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (2)..(2)
<223> OTHER INFORMATION: Xaa at position 2 is Cys or selenocysteine
<220> FEATURE:
<221> NAME/KEY: VARIANT
<222> LOCATION: (3)..(3)
<223> OTHER INFORMATION: Xaa at position 3 is Cys or selenocysteine
<220> FEATURE:
<221> NAME/KEY: VARIANT
<222> LOCATION: (4)..(4)
<223> OTHER INFORMATION: Xaa at position 4 is Ser or Thr
<220> FEATURE:
<221> NAME/KEY: VARIANT
<222> LOCATION: (8)..(8)
<223> OTHER INFORMATION: Xaa at position 8 is Cys or selenocysteine
<220> FEATURE:
<221> NAME/KEY: VARIANT
<222> LOCATION: (9)..(9)
<223> OTHER INFORMATION: Xaa at position 9 is Arg, citrulline, or
      [omega]-nitro-Arg
<220> FEATURE:
<221> NAME/KEY: VARIANT
<222> LOCATION: (10)..(10)
<223> OTHER INFORMATION: Xaa at position 10 is Tyr or mono-iodo-Tyr
<220> FEATURE:
<221> NAME/KEY: VARIANT
<222> LOCATION: (11)..(11)
<223> OTHER INFORMATION: Xaa at position 11 is Arg, Gln, or Glu
<220> FEATURE:
<221> NAME/KEY: VARIANT
<222> LOCATION: (12)..(12)
<223> OTHER INFORMATION: Xaa at position 12 is Cys or selenocysteine
<220> FEATURE:
<221> NAME/KEY: VARIANT
<222> LOCATION: (13)..(13)
<223> OTHER INFORMATION: Xaa at position 13 is Arg
<220> FEATURE:
<221> NAME/KEY: VARIANT
<222> LOCATION: (14)..(14)
<223> OTHER INFORMATION: Xaa at position 14 is Arg
<220> FEATURE:
<221> NAME/KEY: VARIANT
<222> LOCATION: (15)..(15)
<223> OTHER INFORMATION: Xaa at position 15 is Tyr

<400> SEQUENCE: 36

Gly Xaa Xaa Xaa Asp Pro Arg Xaa Xaa Xaa Xaa Xaa Xaa Xaa
1               5                   10                  15
```

```
<210> SEQ ID NO 37
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (2)..(2)
<223> OTHER INFORMATION: Xaa at position 2 is Cys or selenocysteine
<220> FEATURE:
<221> NAME/KEY: VARIANT
<222> LOCATION: (3)..(3)
<223> OTHER INFORMATION: Xaa at position 3 is Cys or selenocysteine
<220> FEATURE:
<221> NAME/KEY: VARIANT
<222> LOCATION: (4)..(4)
<223> OTHER INFORMATION: Xaa at position 4 is Ser or Thr
<220> FEATURE:
<221> NAME/KEY: VARIANT
<222> LOCATION: (8)..(8)
<223> OTHER INFORMATION: Xaa at position 8 is Cys or selenocysteine
<220> FEATURE:
<221> NAME/KEY: VARIANT
<222> LOCATION: (9)..(9)
<223> OTHER INFORMATION: Xaa at position 9 is Arg, citrulline, or
      [omega]-nitro-Arg
<220> FEATURE:
<221> NAME/KEY: VARIANT
<222> LOCATION: (10)..(10)
<223> OTHER INFORMATION: Xaa at position 10 is Tyr or mono-iodo-Tyr
<220> FEATURE:
<221> NAME/KEY: VARIANT
<222> LOCATION: (11)..(11)
<223> OTHER INFORMATION: Xaa at position 11 is Arg, Gln, or Glu
<220> FEATURE:
<221> NAME/KEY: VARIANT
<222> LOCATION: (12)..(12)
<223> OTHER INFORMATION: Xaa at position 12 is Cys or selenocysteine
<220> FEATURE:
<221> NAME/KEY: VARIANT
<222> LOCATION: (13)..(13)
<223> OTHER INFORMATION: Xaa at position 13 is Tyr
<220> FEATURE:
<221> NAME/KEY: VARIANT
<222> LOCATION: (14)..(14)
<223> OTHER INFORMATION: Xaa at position 14 is Arg
<220> FEATURE:
<221> NAME/KEY: VARIANT
<222> LOCATION: (15)..(15)
<223> OTHER INFORMATION: Xaa at position 15 is Arg

<400> SEQUENCE: 37

Gly Xaa Xaa Xaa Asp Pro Arg Xaa Xaa Xaa Xaa Xaa Xaa Xaa Xaa
1               5                   10                  15
```

CONOTOXIN PEPTIDES, PHARMACEUTICAL COMPOSITIONS AND USES THEREOF

CROSS-REFERENCE TO RELATED APPLICATIONS

This application in a U.S. National Phase application based on International Patent Application Serial No. PCT/US2014/040374, filed May 30, 2014, which claims priority to U.S. Provisional Patent Application Ser. No. 61/829,633 filed May 31, 2013, and U.S. Provisional Patent Application Ser. No. 61/843,135 filed Jul. 5, 2013, the entire contents of all of which are incorporated by reference herein.

REFERENCE TO GOVERNMENT SUPPORT

This invention was made with Government support under Grant Nos. P01 MH053631, GM048677, and NS048158 awarded by the National Institutes of Health, The United States Government has certain rights in the invention.

BACKGROUND OF THE DISCLOSURE

Predatory marine snails in the genus *Conus* have venoms that are rich in neuropharmacologically active peptides (Armishaw et al., 2005; Wang et al., 2004; Livett, et al., 2004; Lewis, 2004; Terlau et al., 2004). There are approximately 500 species in *Conus*, and among those that have been examined so far, a conserved feature is the presence of α-conotoxin peptides in their venom. α-Conotoxin peptides are highly disulfide cross-linked peptides with C1-C3 and C2-C4 disulfide bonds.

Due to high sequence variability of their non-cysteine residues, α-conotoxins are extremely diverse and each *Conus* species has a unique complement of α-conotoxin peptides. α-Conotoxin peptides are synthesized as large precursors, and the mature toxin is generated by a proteolytic cleavage toward the C-terminus of the precursor. In contrast to the variable inter-cysteine sequences of the mature toxins, the precursors and the genes encoding them are quite conserved both among α-conotoxin peptides in a given *Conus* species and from species to species.

α-Conotoxin peptides have generally been shown to be nicotinic acetylcholine receptor (nAChR) antagonists (Mcintosh, et al., 1999; Janes, 2005; Dutton et al., 2001; Arias et al., 2000). nAChRs are a group of acetylcholine gated ion channels that are part of the ligand gated ion channel superfamily (Karlin, 2002; Gotti et al., 2004). They are pentamers of transmembrane subunits surrounding a central ion conducting channel. Many different subunits have been identified, and most fall into two main subfamilies (the a subunits and the β subunits). The subunits can associate in various combinations in the receptor pentamers, leading to a diverse family of receptor subtypes. Most of the subtypes contain subunits from both the α and β subunit families, e.g., the human adult muscle subtype contains two a subunits and a β subunit (in addition to a δ and an ε subunit) and the α3β2 subtype is composed of α3 and β2 subunits. nAChRs that are composed of only a subunits are the α7 and α9 subtypes (homopentamers) and the α9α10 subtype (an all α heteropentamer). Phylogenetic analysis shows that the α7, α9, and α10 subunits are more closely related to each other than they are to other nAChR subunits (Le Novere, et al., 2002; Sgard, et al., 2002).

The α9 and α10 nAChR subunits are expressed in diverse tissues. In the inner ear α9α10 nAChRs mediate synaptic transmission between efferent olivocochlear fibers and cochlear hair cells (Sgard, et al., 2002; Elgoyhen, et al., 1994; Elgoyhen, et al., 2001). The α9 and α10 subunits are also found in dorsal root ganglion neurons (Harberger, et al., 2004; Lips, et al., 2002), lymphocytes (Peng, et al., 2004), skin keratinocytes (Arredondo, et al., 2002; Nguyen, et al., 2000; Kurzen, et al., 2004), and the pars tuberalis of the pituitary (Sgard, et al., 2002; Elgoyhen, et al., 1994; Elgoyhen, et al., 2001). In addition, the α9 nAChR subunit is active in breast cancer (Lee, et al., 2010a; Lee, et al., 2010b; Linnoila, 2010). α-Conotoxin peptide RgIA (RgIA; GCCSDPRCRYRCR; SEQ ID NO:1) has been shown to block α9α10 nAChR (Ellison, et al., 2006). Certain analogs of RgIA have also been shown to block α9α10 nAChR (US 2009/0203616, US 2012/0220539, and WO 2008/011006).

SUMMARY OF THE DISCLOSURE

The present disclosure relates to analogs of the α-conotoxin peptide RgIA (analog conotoxin peptides herein). These analog conotoxin peptides block the α9α10 subtype of the nicotinic acetylcholine receptor (nAChR) and can be used for treating pain, inflammatory conditions, inflammation, and/or cancer.

BRIEF DESCRIPTION OF THE FIGURES

FIGS. 1A and 1B show that threonine (Thr or T)56/isoleucine (Ile or I) is responsible for the rat versus human difference in potency of inhibition by RgIA. Mutation of Thr56 to Ile in the rat α9 subunit results in a reduction in RgIA potency on the rat receptor to levels found with the human receptor (FIG. 1A). Replacement of Ile56 with Thr in the human α9 receptor results in an increase in RgIA potency on the human receptor to levels found in rat (FIG. 1B). Values are mean±standard error of the mean (SEM) from at least three oocytes injected with a 1:1 ratio of cRNA from α9 and α10 subunit genes.

FIG. 2 shows that Analog 2 (Table 1; SEQ ID NO:4) selectively blocks α9α10 vs. α7 nAChRs. Analog 2 was applied to Xenopus oocytes expressing human α9α10 or human α7 nAChRs. Analog 2 at 10 nM blocked 75±2.8% of the ACh-evoked response of α9α10 nAChRs. One thousand-fold higher concentration (10 μM peptide) failed to block the α7 nAChRs. (n=5). Representative traces are shown from individual oocytes.

FIG. 3 shows Substance P expression following nerve injury. Photo-micrographs of enhanced expression of substance P in the spinal dorsal horn 24 hours and 1 week following thermal injury.

FIGS. 4A-4J show the efficacy of conotoxin peptides in chemotherapy induced neuropathic pain. Daily administration of RgIA had significant analgesic effects on days 14 and 21 (FIGS. 4A, 4B, 4E, 4F, and 4I). FIGS. 4C, 4D, 4G, 4H, and 4J show data demonstrating an analgesic effect of CSP-4 in this preventive treatment paradigm.

FIGS. 5A and 5B show RgIA (FIG. 5A) and CSP-7 (FIG. 5B) significantly reduced burn-induced thermal hyperalgesia as measured by the Hargraves method at all three doses tested (4, 20 and 100 mcg/Kg).

DETAILED DESCRIPTION

The present disclosure relates to conotoxin peptides that are analogs of the α-conotoxin peptide RgIA (analog conotoxin peptides herein), as well as variants, d-substituted analogs, modifications and derivatives thereof (collectively "conotoxin peptides" herein). These conotoxin peptides block the α9α10 subtype of the nicotinic acetylcholine receptor (nAChR) and can be used to treat pain, inflammatory conditions, inflammation, and/or cancer. The conotoxin peptides can also be used in further drug development as described herein.

I. Analogs of the A-Contoxin Peptide RgIA

Figure 1B:
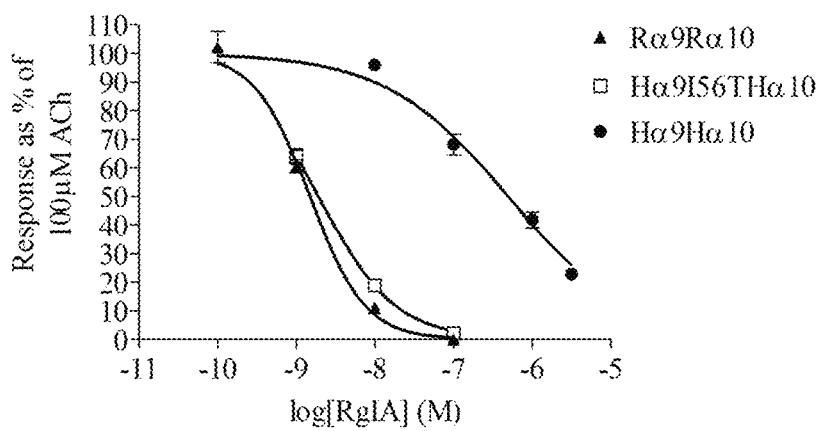

Data from animal pain models coupled with an absence of acute or chronic toxicity suggest that α-conotoxin peptides provide promising leads for drug development. Supporting this conclusion, a related peptide from *Conus victoriae* (Vc1.1) advanced to Phase 2 clinical trials before it was discovered to be significantly less potent on the human versus rat α9α10 nAChR (Livett, et al., 2006). Likewise studies of RgIA have confirmed that this peptide is ~170-fold less potent on the human versus rat receptor (Azam et al., 2012). Using site-directed mutagenesis, a single residue (Thr/Ile56) in the α9 subunit has been identified that accounted for most of the difference in interaction between rat and human α9α10 and RgIA (FIG. 1A). Altering the human α9 from Ile56 to the Thr found in rats resulted in a 2 log increase in RgIA potency on the human receptor (FIG. 1B).

Using knowledge of receptor-ligand dynamics together with the nuclear magnetic resonance (NMR) structure of RgIA, structural analogs of RgIA that are roughly equipotent on the human and rat receptors were designed. Four mutations in RgIA were identified that enhanced human α9α10 binding. Single substitutions of arginine (Arg or R)9 to either citrulline or w-nitro-Arg, and tyrosine (Tyr or Y)10 to mono-iodo-Tyr (SEQ ID NO:21 for the latter) each resulted in a small increase in potency on the rat receptor, but a 4-8 fold increase in potency on the human receptor. Alteration of serine (Ser or S)4 to Thr, or Arg11 to glutamine (Gln or Q) also resulted in a 3-4 fold increase each in potency on the human receptor. Combining these four alterations together in a single peptide (Analog 2; SEQ ID NO:19) resulted in a >100-fold increase in potency on the human receptor with an $IC_{50}$~8 nM (Table 2).

Further optimization of Analog 2 demonstrated that improved potency on the human receptor could be achieved by the further addition of two Arg residues to the end of the peptide (Analog 4; SEQ ID NO:4) and/or by modification of Arg13 to Tyr (Analog 3; SEQ ID NO:3). In addition to these substitutions, two of the cysteine (Cys or C) residues (Cys2 and Cys3) were also modified to selenocysteine to enhance peptide stability and refolding efficiency (SEQ ID NO:20). The double selenocysteine mutant demonstrated a 10-fold increase in potency on the human receptor relative to unmodified RgIA. The above changes to RgIA, alone or in combination, have been used to construct analogs with enhanced potency on the human channel, solving the key developmental problem of the previous clinical candidate Vc1.1.

In various embodiments, analog conotoxin peptides disclosed herein have the formula GX6X7X3DPRX8X1X2X4X9X5 (SEQ ID NO:22, SEQ ID NO:30 to SEQ ID NO:37), wherein X1 is Arg, citrulline, or ω-nitro-Arg; X2 is Tyr or mono-iodo-Tyr; X3 is Ser or Thr; X4 is Arg, Gln, or Glu; X5 is Arg, Tyr, phenylalanine (Phe or F), tryptophan (Trp or W), Tyr-Tyr, Tyr-Arg, Arg-Arg-Arg, Arg-Arg-Tyr, or Tyr-Arg-Arg; X6 is Cys or selenocysteine; X7 is Cys or selenocysteine; X8 is Cys or selenocysteine; and X9 is Cys or selenocysteine. In one embodiment, X1 is Arg. In one embodiment, X1 is citrulline. In one embodiment, X1 is ω-nitro-Arg. In one embodiment, X3 is Ser. In one embodiment, X3 is Thr. In one embodiment, X4 is Arg. In one embodiment, X4 is Gln. In one embodiment, X4 is Glu. In one embodiment, X5 is Arg. In one embodiment, X5 is Tyr. In one embodiment, X5 is Phe. In one embodiment, X5 is Trp. In one embodiment, X5 is Tyr-Tyr. In one embodiment, X5 is Tyr-Arg. In one embodiment, X5 is Arg-Arg-Arg. In one embodiment, X5 is Arg-Arg-Tyr. In one embodiment, X5 is Tyr-Arg-Arg. In one embodiment, X6 is Cys. In one embodiment, X6 is selenocysteine. In one embodiment, X7 is Cys. In one embodiment, X7 is selenocysteine. In one embodiment, X8 is Cys. In one embodiment, X8 is selenocysteine. In one embodiment, X9 is Cys. In one embodiment, X9 is selenocysteine.

In various embodiments, analog conotoxin peptides disclosed herein have the formula GCCTDPRCX1X2QCX3 (SEQ ID NO:2, SEQ ID NO:23 to SEQ ID NO:29), wherein X1 is Arg or citrulline; X2 is mono-iodo-Tyr; and X3 is Tyr, Phe, Trp, Tyr-Tyr, Tyr-Arg, Arg-Arg-Arg, Arg-Arg-Tyr, or Tyr-Arg-Arg. In one embodiment, X1 is Arg. In another embodiment, X1 is citrulline. In one embodiment, X3 is Tyr. In another embodiment, X3 is Phe. In another embodiment, X3 is Trp. In another embodiment, X3 is Tyr-Tyr. In another embodiment, X3 is Tyr-Arg. In another embodiment, X3 is Arg-Arg-Arg. In another embodiment, X3 is Arg-Arg-Tyr. In another embodiment, X3 is Tyr-Arg-Arg.

In one embodiment, the analog conotoxin peptide has the formula GCCTDPRCX1X2QCY (SEQ ID NO:3; also referred to herein as Analog 3), wherein X1 is citrulline and X2 is mono-iodo-Tyr. In another embodiment, the analog conotoxin peptide has the formula GCCTDPRCX1X2QCRRR (SEQ ID NO:4; also referred to herein as Analog 4), wherein X1 is citrulline and X2 is mono-iodo-Tyr. In an additional embodiment, the analog conotoxin peptide has the formula GCCTDPRCX1X2QCYRR (SEQ ID NO:5; also referred to herein as Analog 5), wherein X1 is citrulline and X2 is mono-iodo-Tyr. In a further embodiment, the analog conotoxin peptide has the formula GCCTDPRCX1X2QCRRY (SEQ ID NO:6; also referred to herein as Analog 6), wherein X1 is citrulline and X2 is mono-iodo-Tyr. In another embodiment, the analog conotoxin peptide has the formula GCCTDPRCX1X2QCF (SEQ ID NO:7; also referred to herein as Analog 7), wherein X1 is citrulline and X2 is mono-iodo-Tyr. In an additional embodiment, the analog conotoxin peptide has the formula GCCTDPRCX1X2QCW (SEQ ID NO:8; also referred to herein as Analog 8), wherein X1 is citrulline and X2 is mono-iodo-Tyr. In a further embodiment, the analog conotoxin peptide has the formula GCCTDPRCX1X2QCYY (SEQ ID NO:9; also referred to herein as Analog 9), wherein X1 is citrulline and X2 is mono-iodo-Tyr. In another embodiment, the analog conotoxin peptide has the formula GCCTDPRCX1X2QCYR (SEQ ID NO:10; also referred to herein as Analog 10), wherein X1 is citrulline and X2 is mono-iodo-Tyr.

In one embodiment, the analog conotoxin peptide has the formula GCCTDPRCRX2QCY (SEQ ID NO:11; also referred to herein as Analog 11), wherein X2 is mono-iodo-Tyr. In another embodiment, the analog conotoxin peptide has the formula GCCTDPRCRX2QCRRR (SEQ ID NO:12; also referred to herein as Analog 12), wherein X2 is mono-iodo-Tyr. In an additional embodiment, the analog conotoxin peptide has the formula GCCTDPRCRX2QCYRR (SEQ ID NO:13; also referred to herein as Analog 13), wherein X2 is mono-iodo-Tyr. In a further embodiment, the analog conotoxin peptide has the formula GCCTDPRCRX2QCRRY (SEQ ID NO:14; also referred to herein as Analog 14), wherein X2 is mono-iodo-Tyr. In another embodiment, the analog conotoxin peptide has the formula GCCTDPRCRX2QCF (SEQ ID NO:15; also referred to herein as Analog 15), wherein X2 is mono-iodo-Tyr. In an additional embodiment, the analog conotoxin peptide has the formula GCCTDPRCRX2QCW (SEQ ID NO:16; also referred to herein as Analog 16), wherein X2 is mono-iodo-Tyr. In a further embodiment, the analog conotoxin peptide has the formula GCCTDPRCRX2QCYY (SEQ ID NO:17; also referred to herein as Analog 17), wherein X2 is mono-iodo-Tyr. In another embodiment, the analog conotoxin peptide has the formula GCCTDPRCRX2QCYR (SEQ ID NO:18; also referred to herein as Analog 18), wherein X2 is mono-iodo-Tyr.

"Variants" of analog conotoxin peptides disclosed herein include peptides having one or more amino acid additions, deletions, stop positions, or substitutions, as compared to an analog conotoxin peptide disclosed herein.

An amino acid substitution can be a conservative or a non-conservative substitution. Variants of analog conotoxin peptides disclosed herein can include those having one or more conservative amino acid substitutions. As used herein, a "conservative substitution" involves a substitution found in one of the following conservative substitutions groups: Group 1: alanine (Ala or A), glycine (Gly or G), Ser, Thr; Group 2: aspartic acid (Asp or D), Glu; Group 3: asparagine (Asn or N), glutamine (Gln or Q); Group 4: Arg, lysine (Lys or K), histidine (His or H); Group 5: Ile, leucine (Leu or L), methionine (Met or M), valine (Val or V); and Group 6: Phe, Tyr, Trp.

Additionally, amino acids can be grouped into conservative substitution groups by similar function, chemical structure, or composition (e.g., acidic, basic, aliphatic, aromatic, sulfur-containing). For example, an aliphatic grouping may include, for purposes of substitution, Gly, Ala, Val, Leu, and Ile. Other groups containing amino acids that are considered conservative substitutions for one another include: sulfur-containing: Met and Cys; acidic: Asp, Glu, Asn, and Gln; small aliphatic, nonpolar or slightly polar residues: Ala, Ser, Thr, Pro, and Gly; polar, negatively charged residues and their amides: Asp, Asn, Glu, and Gln; polar, positively charged residues: His, Arg, and Lys; large aliphatic, nonpolar residues: Met, Leu, Ile, Val, and Cys; and large aromatic residues: Phe, Tyr, and Trp. Additional information is found in Creighton (1984) Proteins, W.H. Freeman and Company.

Variants of analog conotoxin peptide sequences disclosed or referenced herein also include sequences with at least 70% sequence identity, at least 80% sequence identity, at least 85% sequence, at least 90% sequence identity, at least 95% sequence identity, at least 96% sequence identity, at least 97% sequence identity, at least 98% sequence identity, or at least 99% sequence identity to a peptide sequence disclosed or referenced herein. More particularly, variants of the analog conotoxin peptides disclosed herein include peptides that share: 70% sequence identity with any of SEQ ID NO:1-37; 80% sequence identity with any of SEQ ID NO: 1-37; 81% sequence identity with any of SEQ ID NO: 1-37; 82% sequence identity with any of SEQ ID NO: 1-37; 83% sequence identity with any of SEQ ID NO: 1-37; 84% sequence identity with any of SEQ ID NO: 1-37; 85% sequence identity with any of SEQ ID NO: 1-37; 86% sequence identity with any of SEQ ID NO: 1-37; 87% sequence identity with any of SEQ ID NO: 1-37; 88% sequence identity with any of SEQ ID NO: 1-37; 89% sequence identity with any of SEQ ID NO: 1-37; 90% sequence identity with any of SEQ ID NO: 1-37; 91% sequence identity with any of SEQ ID NO: 1-37; 92% sequence identity with any of SEQ ID NO: 1-37; 93% sequence identity with any of SEQ ID NO: 1-37; 94% sequence identity with any of SEQ ID NO: 1-37; 95% sequence identity with any of SEQ ID NO: 1-37; 96% sequence identity with any of SEQ ID NO: 1-37; 97% sequence identity with any of SEQ ID NO: 1-37; 98% sequence identity with any of SEQ ID NO: 1-37; or 99% sequence identity with any of SEQ ID NO: 1-37.

"% sequence identity" refers to a relationship between two or more sequences, as determined by comparing the sequences. In the art, "identity" also means the degree of sequence relatedness between peptide sequences as determined by the match between strings of such sequences. "Identity" (often referred to as "similarity") can be readily calculated by known methods, including those described in: Computational Molecular Biology (Lesk, A. M., ed.) Oxford University Press, N Y (1988); Biocomputing: Informatics and Genome Projects (Smith, D. W., ed.) Academic Press, N Y (1994); Computer Analysis of Sequence Data, Part I (Griffin, A. M., and Griffin, H. G., eds.) Humana Press, N J (1994); Sequence Analysis in Molecular Biology (Von Heijne, G., ed.) Academic Press (1987); and Sequence Analysis Primer (Gribskov, M. and Devereux, J., eds.) Oxford University Press, NY (1992). Preferred methods to determine sequence identity are designed to give the best match between the sequences tested. Methods to determine sequence identity and similarity are codified in publicly available computer programs. Sequence alignments and percent identity calculations may be performed using the Megalign program of the LASERGENE bioinformatics computing suite (DNASTAR, Inc., Madison, Wis.). Multiple alignment of the sequences can also be performed using the Clustal method of alignment (Higgins and Sharp CABIOS, 5, 151-153 (1989) with default parameters (GAP PENALTY=10, GAP LENGTH PENALTY=10). Relevant programs also include the GCG suite of programs (Wisconsin Package Version 9.0, Genetics Computer Group (GCG), Madison, Wis.); BLASTP, BLASTN, BLASTX (Altschul, et al., J. Mol. Biol. 215:403-410 (1990); DNASTAR (DNASTAR, Inc., Madison, Wis.); and the FASTA program incorporating the Smith-Waterman algorithm (Pearson, Comput. Methods Genome Res., [Proc. Int. Symp.] (1994), Meeting Date 1992, 111-20. Editor(s): Suhai, Sandor. Publisher: Plenum, New York, N.Y. Within the context of this disclosure it will be understood that where sequence analysis software is used for analysis, the results of the analysis are based on the "default values" of the program referenced. As used herein "default values" will mean any set of values or parameters which originally load with the software when first initialized.

"D-substituted analogs" include analog conotoxin peptides disclosed herein having one more L-amino acids substituted with D-amino acids. The D-amino acid can be the same amino acid type as that found in the analog sequence or can be a different amino acid. Accordingly, D-analogs are also variants.

"Modifications" include analog conotoxin peptides disclosed herein wherein one or more amino acids have been replaced with a non-amino acid component, or where the amino acid has been conjugated to a functional group or a functional group has been otherwise associated with an amino acid. The modified amino acid may be, e.g., a glycosylated amino acid, a PEGylated amino acid, a farnesylated amino acid, an acetylated amino acid, a biotinylated amino acid, an amino acid conjugated to a lipid moiety, or an amino acid conjugated to an organic derivatizing agent. The presence of modified amino acids may be advantageous in, for example, (a) increasing polypeptide serum half-life and/or functional in vivo half-life, (b) reducing polypeptide antigenicity, (c) increasing polypeptide storage stability, (d) increasing peptide solubility, (e) prolonging circulating time, and/or (f) increasing bioavailability, e.g., increasing the area under the curve ($AUC_{sc}$). Amino acid(s) can be modified, for example, co-translationally or post-translationally during recombinant production (e.g., N-linked glycosylation at N-X-S/T motifs during expression in mammalian cells) or modified by synthetic means. The modified amino acid can be within the sequence or at the terminal end of a sequence. Modifications can include derivatives as described elsewhere herein.

The C-terminus may be a carboxylic acid or an amide group, preferably a carboxylic acid group for each of the conotoxin peptides. The present disclosure also relates to the analog conotoxin peptides further modified by (i) additions made to the C-terminus, such as Tyr, iodo-Tyr, a fluorescent tag, or (ii) additions made to the N-terminus, such as Tyr, iodo-Tyr, pyroglutamate, or a fluorescent tag.

In addition, residues or groups of residues known to the skilled artisan to improve stability can be added to the C-terminus and/or N-terminus. Also, residues or groups of residues known to the skilled artisan to improve oral availability can be added to the C-terminus and/or N-terminus.

The present disclosure is further directed to derivatives of the disclosed analog conotoxin peptides. Derivatives include analog conotoxin peptides having acylic permutations in which the cyclic permutants retain the native bridging pattern of native conotoxin peptide (Craik, et al., (2001), e.g., a cyclized conotoxin peptide having an amide cyclized backbone such that the conotoxin peptide has no free N- or C-terminus in which the conotoxin peptide includes the native disulfide bonds (U.S. Pat. No. 7,312,195)). In one embodiment, the cyclized conotoxin peptide includes a linear conotoxin peptide and a peptide linker, wherein the N- and C-termini of the linear conotoxin peptide are linked via the peptide linker to form the amide cyclized peptide backbone. In some embodiments, the peptide linker includes amino acids selected from Gly, Ala, and combinations thereof.

Various cyclization methods can be applied to the analog conotoxin peptides described herein. The analog conotoxin peptides described herein can be readily cyclized using alanine bridges. (Clark, et al., 2013; Clark, et al., 2012). Cyclizing analog conotoxin peptides can improve their oral bioavailability and reduce the susceptibility to proteolysis, without affecting the affinity of the analog conotoxin peptides for their specific targets.

Embodiments disclosed herein include the analog conotoxin peptides described herein as well as variants, D-substituted analogs, modifications, and derivatives of the analog conotoxin peptides described herein. In some embodiments, variants, D-substituted analogs, modifications, and derivatives have 1, 2, 3, 4, 5, 6, 7, 8, 9, 10, 11, 12, 13, 14, 15, 16, 17, or 18 sequence additions, deletions; stop positions, substitutions, replacements, conjugations, associations, or permutations. In additional embodiments an Xaa position can be included in any position of an analog conotoxin peptide, wherein Xaa represents an addition, deletion, stop position, substitution, replacement, conjugation; association, or permutation.

Each conotoxin peptide disclosed herein may also include additions, deletions, stop positions, substitutions, replacements, conjugations, associations, or permutations at any position including positions 1, 2, 3, 4, 5, 6, 7, 8, 9, 10, 11, 12, 13, 14, 15, 16, 17, or 18 of an analog conotoxin peptide sequence disclosed herein. Accordingly, in particular embodiments each amino acid position of each analog conotoxin peptide can be an Xaa position wherein Xaa denotes an addition, deletion, stop position, substitution, replacement, conjugation, association or permutation of the amino acid at the particular position. In particular embodiments, each analog conotoxin peptide has 1, 2, 3, 4, 5, 6, 7, 8, 9, 10, 11, 12, 13, 14, 15, 16, 17, or 18 Xaa positions at one or more of positions 1, 2, 3, 4, 5, 6, 7, 8, 9, 10, 11, 12, 13, 14, 15, 16, 17. or 18.

An analog can have more than one change (addition, deletion, stop position, substitution, replacement, conjugation, association or permutation) and qualify as one or more of a variant, D-substituted analog, modification and/or derivative. That is, inclusion of one classification of analog, variant, D-substituted analog, modification and/or derivative is not exclusive to inclusion in other classifications and all are collectively referred to as "conotoxin peptides" herein.

As stated, conotoxin peptides disclosed herein block the α9α10 subtype of the nAChR. Blocking can be measured by any effective means. In one embodiment, blocking is measured as the displacement of labeled RgIA from the α9α10 subtype of the nAChR by a conotoxin peptide disclosed herein. In one embodiment, blocking can be a 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% displacement of labeled RgIA from the α9α10 subtype of the nAChR by a conotoxin peptide disclosed herein. In a second embodiment, blocking can be measured by conducting a biological assay on a conotoxin peptide disclosed herein to determine its therapeutic activity as compared to the results obtained from the biological assay of RgIA. In one embodiment, blocking can be 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% greater therapeutic activity of conotoxin peptide disclosed herein when compared to RgIA as measured by the biological assay. In a third embodiment, the binding affinity of a conotoxin peptide disclosed herein to the α9α10 subtype of the nAChR can be measured and compared to the binding affinity of RgIA to the α9α10 subtype of the nAChR. In one embodiment, blocking can be a 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% greater binding affinity of the conotoxin peptide disclosed herein over RgIA. In a fourth embodiment, the effect of a conotoxin peptide disclosed herein on the function of the α9α10 subtype of the nAChR is analyzed by measuring the effect in functional assays, such as electrophysiological assays, calcium imaging assays, and the like. In one embodiment, blocking includes a 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% reduction in the function of the α9α10 subtype of the nAChR as measured by a functional assay when compared to RgIA.

The conotoxin peptides can be prepared using recombinant DNA technology. Conotoxin peptides may also be prepared using the Merrifield solid-phase synthesis, although other equivalent chemical syntheses known in the art can also be used. Solid-phase synthesis is commenced from the C-terminus of the conotoxin peptide by coupling a protected α-amino acid to a suitable resin. Such a starting material can be prepared by attaching an α-amino-protected amino acid by an ester linkage to a chloromethylated resin or a hydroxymethyl resin, or by an amide bond to a benzhydrylamine (BHA) resin or para-methylbenzhydrylamine (MBHA) resin. Preparation of the hydroxymethyl resin is described by Bodansky et al., (1966). Chloromethylated resins are commercially available from Bio Rad Laboratories (Richmond, Calif.) and from Lab. Systems, Inc. The preparation of such a resin is described by Stewart and Young (1969). BHA and MBHA resin supports are commercially available, and are generally used when the desired conotoxin peptide being synthesized has an unsubstituted amide at the C-terminus. Thus, solid resin supports may be any of those known in the art, such as one having the formulae —O—CH2-resin support, —NH BHA resin support, or —NH-MBHA resin support. When the unsubstituted amide is desired, use of a BHA or MBHA resin can be advantageous because cleavage directly gives the amide. In case the N-methyl amide is desired, it can be generated from an N-methyl BHA resin. Should other substituted amides be desired, the teaching of U.S. Pat. No. 4,569,967 can be used, or should still other groups than the free acid be desired at the C-terminus, it may be preferable to synthesize the conotoxin peptide using classical methods as set forth in the Houben-Weyl text (1974).

The C-terminal amino acid, protected by Boc or Fmoc and by a side-chain protecting group, if appropriate, can be first coupled to a chloromethylated resin according to the procedure set forth in Horiki et al., (1978), using KF in dimethylformamide (DMF) at about 60° C. for 24 hours with stirring, when a conotoxin peptide having free acid at the C-terminus is to be synthesized. Following the coupling of the BOC-protected amino acid to the resin support, the α-amino protecting group can be removed, as by using trifluoroacetic acid (TFA) in methylene chloride or TFA alone. The deprotection can be carried out at a temperature between 0° C. and room temperature. Other standard cleaving reagents, such as HCl in dioxane, and conditions for removal of specific α-amino protecting groups may be used as described in Schroder & Lubke (1965).

After removal of the α-amino-protecting group, the remaining α-amino- and side chain-protected amino acids can be coupled step-wise in the desired order to obtain an intermediate compound or as an alternative to adding each amino acid separately in the synthesis, some of them may be coupled to one another prior to addition to the solid phase reactor. Selection of an appropriate coupling reagent is within the skill of the art. Exemplary coupling reagents include N,N'-dicyclohexylcarbodiimide (DCC, DIC, HBTU, HATU, TBTU in the presence of HoBt or HoAt).

The activating reagents used in the solid phase synthesis of peptides including conotoxin peptides are well known in the art. Examples of suitable activating reagents include carbodiimides, such as N,N'-diisopropylcarbodiimide and N-ethyl-N'-(3-dimethylaminopropyl)carbodiimide. Other activating reagents and their use in peptide coupling are described by Schroder & Lubke (1965) and Kapoor (1970).

Each protected amino acid or amino acid sequence can be introduced into the solid-phase reactor in a twofold or more excess, and the coupling may be carried out in a medium of DMF:$CH_2Cl_2$ (1:1) or in DMF or $CH_2Cl_2$ alone. In cases where intermediate coupling occurs, the coupling procedure can be repeated before removal of the α-amino protecting group prior to the coupling of the next amino acid. The success of the coupling reaction at each stage of the synthesis, if performed manually, can be monitored by the ninhydrin reaction, as described by Kaiser, et al., (1970). Coupling reactions can be performed automatically, as on a Beckman 990 automatic synthesizer, using a program such as that reported in Rivier, et al., (1978).

After the desired amino acid sequence has been completed, the intermediate peptide can be removed from the resin support by treatment with a reagent, such as liquid hydrogen fluoride or TFA (if using Fmoc chemistry), which not only cleaves the peptide from the resin but also cleaves all remaining side chain protecting groups and also the α-amino protecting group at the N-terminus if it was not previously removed to obtain the peptide in the form of the free acid. If Met is present in the sequence, the Boc protecting group can be first removed using TFA/ethanedithiol prior to cleaving the peptide from the resin with HF to eliminate potential S-alkylation. When using hydrogen fluoride or TFA for cleaving, one or more scavengers such as anisole, cresol, dimethyl sulfide and methylethyl sulfide can be included in the reaction vessel.

Cyclization of the linear conotoxin peptide can be affected, as opposed to cyclizing the conotoxin peptide while a part of the peptido-resin, to create bonds between Cys residues. To effect such a disulfide cyclizing linkage, a fully protected conotoxin peptide can be cleaved from a hydroxymethylated resin or a chloromethylated resin support by ammonolysis, as is well known in the art, to yield the fully protected amide intermediate, which is thereafter suitably cyclized and deprotected. Alternatively, deprotection, as well as cleavage of the conotoxin peptide from the above resins or a benzhydrylamine (BHA) resin or a methylbenzhydrylamine (MBHA), can take place at 0° C. with hydrofluoric acid (HF) or TFA, followed by oxidation as described above.

The conotoxin peptides can also be synthesized using an automatic synthesizer. In these embodiments, amino acids can be sequentially coupled to an MBHA Rink resin (typically 100 mg of resin) beginning at the C-terminus using an Advanced Chemtech 357 Automatic Peptide Synthesizer. Couplings are carried out using 1,3-diisopropylcarbodimide in N-methylpyrrolidinone (NMP) or by 2-(1H-benzotriazole-1-yl)-1,1,3,3-tetramethyluronium hexafluorophosphate (HBTU) and diethylisopropylethylamine (DIEA). The Fmoc protecting group can be removed by treatment with a 20% solution of piperidine in dimethylformamide (DMF). Resins are subsequently washed with DMF (twice), followed by methanol and NMP.

II. Methods of Use

A. Methods of Treatment

The conotoxin peptides of the present disclosure are useful in methods of treating conditions associated with the α9α10 receptor subtype of the nicotinic acetylcholine receptor (nAChR) in a subject. Such methods include administering to a subject in need thereof a therapeutically effective amount of a disclosed conotoxin peptide or a pharmaceutically acceptable salt thereof, wherein the disclosed conotoxin peptide blocks the α9α10 subtype of the nAChR.

The activity of certain α-conotoxins, including RgIA and its analogs, in blocking the α9α10 subtype of nAChR has been shown herein in studies using oocytes that express different subtypes of the nAChR (Ellison et al., 2006; Vincler et al., 2006; WO 2008/011006; US 2009/0203616; US 2012/0220539). The activity of α-conotoxins, including RgIA, as an antinocieceptive and an analgesic has been shown in studies of chronic constriction injury (Vincler, et al., 2006; WO2008/011006; US2009/0203616). The activity of α-conotoxins, including RgIA, in inhibiting migration of immune cells has been shown in studies of chronic constriction injury (Vincler, et al., 2006; WO2008/011006; US2009/0203616).

Conotoxin peptides that block the α9α10 subtype of nAChR are useful for treating pain, for treating inflammation and/or inflammatory conditions and for treating cancers. In certain embodiments, the conotoxin peptides are effective based on their ability to inhibit the migration of immune cells. In other embodiments, the compounds are effective based on their ability to slow demyelination and/or increase the number of intact nerve fibers.

Exemplary types of pain that can be treated include general pain, chronic pain, neuropathic pain, nociceptive pain, and inflammatory pain. In addition, these types of pain can be associated with and/or induced by causes including: peripheral nerve or nociceptor damage, inflammatory disorders, metabolic disorders, virus infection, cancers, pain induced by chemotherapeutic agents, pain induced after surgical procedure, and pain induced by burn or other physical tissue injury.

Exemplary inflammatory conditions that can be treated include inflammation, chronic inflammation, rheumatic diseases (including arthritis, lupus, ankylosing spondylitis, fibromyalgia, tendonitis, bursitis, scleroderma, and gout), sepsis, fibromyalgia, inflammatory bowel disease (including ulcerative colitis and Crohn's disease), sarcoidosis, endometriosis, uterine fibroids, inflammatory skin diseases (including psoriasis and impaired wound healing), inflammatory conditions of the lungs (including asthma and chronic obstructive pulmonary disease), diseases associated with inflammation of the nervous system (including Parkinson's Disease and Alzheimer's Disease), periodontal disease, and cardiovascular disease.

Exemplary cancers that can be treated include breast cancers. α9-nAChR is overexpressed in human breast tumor tissue (Lee et al., 2010(a)) and receptor inhibition by siRNA or other mechanism reduced in vitro and in vivo carcinogenic properties of breast cancer cells, including inhibition of cancer cell proliferation (Chen et al., 2011). In certain embodiments, RgIA analogs are used in therapeutic amounts in order to inhibit tumor growth by inhibition of α9-nAChR.

Methods disclosed herein include treating subjects (humans, veterinary animals (dogs, cats, reptiles, birds, etc.), livestock (horses, cattle, goats, pigs, chickens, etc.), and research animals (monkeys, rats, mice, fish, etc.) with conotoxin peptides disclosed herein including pharmaceutically-acceptable salts and prodrugs thereof. Treating subjects includes delivering therapeutically effective amounts of the disclosed conotoxin peptides. Therapeutically effective amounts include those that provide effective amounts, prophylactic treatments, and/or therapeutic treatments.

An "effective amount" is the amount of a conotoxin peptide necessary to result in a desired physiological change in the subject. Effective amounts are often administered for research purposes. Effective amounts disclosed herein result in a desired physiological change in a research assay intended to study the effectiveness of a conotoxin peptide in the treatment of pain, inflammatory conditions, inflammation and/or cancer.

A "prophylactic treatment" includes a treatment administered to a subject who does not display signs or symptoms pain, an inflammatory condition, inflammation and/or cancer or displays only early signs or symptoms of pain, an inflammatory condition, inflammation and/or cancer such that treatment is administered for the purpose of diminishing, preventing, or decreasing the risk of developing the pain, inflammatory condition, inflammation and/or cancer further. Thus, a prophylactic treatment functions as a preventative treatment against pain, an inflammatory condition, inflammation and/or cancer.

A "therapeutic treatment" includes a treatment administered to a subject who displays symptoms or signs of pain, an inflammatory condition, inflammation and/or cancer and is administered to the subject for the purpose of diminishing or eliminating those signs or symptoms of the pain, inflammatory condition, inflammation and/or cancer. The therapeutic treatment can reduce, control, or eliminate the presence or activity of pain, an inflammatory condition, inflammation and/or cancer and/or reduce control or eliminate side effects of pain, an inflammatory condition, inflammation and/or cancer.

Therapeutically effective amounts in the treatment of chemotherapy-induced neuropathic pain (CINP) can include those that decrease mechanical hyperalgesia, mechanical allodynia, thermal (heat-induced) hyperalgesia, thermal (cold-induced) allodynia, the number of migrating immune cells, levels of inflammatory mediators, and/or subject-reported subjective pain levels.

Therapeutically effective amounts in the treatment of burn-induced neuropathic pain can include those that decrease mechanical hyperalgesia, mechanical allodynia, thermal (heat-induced) hyperalgesia, thermal (cold-induced) allodynia, the number of migrating immune cells, levels of inflammatory mediators, and/or subject-reported subjective pain levels.

Therapeutically effective amounts in the treatment of post-operative neuropathic pain can include those that decrease mechanical hyperalgesia, mechanical allodynia, thermal (heat-induced) hyperalgesia, thermal (cold-induced) allodynia, the number of migrating immune cells, levels of inflammatory mediators, and/or subject-reported subjective pain levels.

Therapeutically effective amounts in the treatment of inflammatory disorders can include those that decrease levels of inflammatory markers at the gene expression or protein level and/or reduce the number of migrating immune cells. In addition, pain associated with inflammatory disorders can be treated by therapeutically effective amounts that result in the decrease of mechanical hyperalgesia, mechanical allodynia, thermal (heat-induced) hyperalgesia, thermal (cold-induced) allodynia, and/or subject-reported subjective pain levels.

Therapeutically effective amounts in the treatment of cancers, such as breast cancers, can include those that decrease a number of tumor cells, decrease the number of metastases, decrease tumor volume, increase life expectancy, induce apoptosis of cancer cells, induce cancer cell death, induce chemo- or radiosensitivity in cancer cells, inhibit angiogenesis near cancer cells, inhibit cancer cell proliferation cells, inhibit tumor growth cells, prevent metastasis, prolong a subject's life, reduce cancer-associated pain, and/or reduce relapse or re-occurrence of the cancer in a subject following treatment.

For administration, therapeutically effective amounts (also referred to herein as doses) can be initially estimated based on results from in vitro assays and/or animal model studies. For example, a dose can be formulated in animal models to achieve a circulating concentration range that includes an $IC_{50}$ as determined in cell culture against a particular target. Such information can be used to more accurately determine useful doses in subjects of interest.

The actual amount administered to a particular subject as a therapeutically effective amount can be determined by a physician, veterinarian, or researcher taking into account parameters such as physical and physiological factors including target, body weight, severity of condition, type of pain, inflammatory condition or cancer, previous or concurrent therapeutic interventions, idiopathy of the subject, and route of administration.

Dosage may be adjusted appropriately to achieve desired conotoxin peptide levels, locally or systemically. Typically the conotoxin peptides of the present disclosure exhibit their effect at a dosage range from 0.001 mg/kg to 250 mg/kg, preferably from 0.01 mg/kg to 100 mg/kg of the conotoxin peptide, more preferably from 0.05 mg/kg to 75 mg/kg. A suitable dose can be administered in multiple sub-doses per day. Typically, a dose or sub-dose may contain from 0.1 mg to 500 mg of the conotoxin peptide per unit dosage form. A more preferred dosage will contain from 0.5 mg to 100 mg of conotoxin peptide per unit dosage form.

Additional useful doses can often range from 0.1 to 5 μg/kg or from 0.5 to 1 μg/kg. In other examples, a dose can include 1 μg/kg, 5 μg/kg, 10 μg/kg, 15 μg/kg, 20 μg/kg, 25 μg/kg, 30 μg/kg, 35 μg/kg, 40 μg/kg, 45 μg/kg, 50 μg/kg, 55 μg/kg, 60 μg/kg, 65 μg/kg, 70 μg/kg, 75 μg/kg, 80 μg/kg, 85 μg/kg, 90 μg/kg, 95 μg/kg, 100 μg/kg, 150 μg/kg, 200 μg/kg, 250 μg/kg, 350 μg/kg, 400 μg/kg, 450 μg/kg, 500 μg/kg, 550 μg/kg, 600 μg/kg, 650 μg/kg, 700 μg/kg, 750 μg/kg, 800 μg/kg, 850 μg/kg, 900 μg/kg, 950 μg/kg, 1000 μg/kg, 0.1 to 5 mg/kg, or from 0.5 to 1 mg/kg. In other examples, a dose can include 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, 100 mg/kg, 150 mg/kg, 200 mg/kg, 250 mg/kg, 350 mg/kg, 400 mg/kg, 450 mg/kg, 500 mg/kg, 550 mg/kg, 600 mg/kg, 650 mg/kg, 700 mg/kg, 750 mg/kg, 800 mg/kg, 850 mg/kg, 900 mg/kg, 950 mg/kg, 1000 mg/kg, or more.

In particular embodiments, dosages can be initiated at lower levels and increased until desired effects are achieved. In the event that the response in a subject is insufficient at such doses, even higher doses (or effective higher doses by a different, more localized delivery route) may be employed to the extent that subject tolerance permits. Continuous dosing over, for example, 24 hours or multiple doses per day are contemplated to achieve appropriate systemic levels of conotoxin peptide.

Therapeutically effective amounts can be achieved by administering single or multiple doses during the course of a treatment regimen (e.g., daily, every other day, every 3 days, every 4 days, every 5 days, every 6 days, weekly, every 2 weeks, every 3 weeks, monthly, every 2 months, every 3 months, every 4 months, every 5 months, every 6 months, every 7 months, every 8 months, every 9 months, every 10 months, every 11 month, or yearly.

A variety of administration routes are available. The particular mode selected can depend upon the particular conotoxin peptide delivered, the severity of pain, inflammatory condition or cancer being treated, and the dosage required to provide a therapeutically effective amount. Any mode of administration that is medically acceptable, meaning any mode that provides a therapeutically effective amount of the conotoxin peptide without causing clinically unacceptable adverse effects that outweigh the benefits of administration according to sound medical judgment can be used. Exemplary routes of administration include intravenous, intradermal, intraarterial, intraparenteral, intranasal, intranodal, intralymphatic, intraperitoneal, intralesional, intraprostatic, intravaginal, intrarectal, topical, intrathecal, intratumoral, intramuscular, intravesicular, oral, subcutaneous, and/or sublingual administration and more particularly by intravenous, intradermal, intraarterial, intraparenteral, intranasal, intranodal, intralymphatic, intraperitoneal, intralesional, intraprostatic, intravaginal, intrarectal, topical, intrathecal, intratumoral, intramuscular, intravesicular, oral, subcutaneous, and/or sublingual injection.

In one embodiment, the conotoxin peptide is delivered directly into the central nervous system (CNS), preferably to the brain ventricles, brain parenchyma, the intrathecal space, or other suitable CNS location.

Alternatively, targeting therapies may be used to deliver the conotoxin peptide more specifically to certain types of cell, by the use of targeting systems such as antibodies or cell specific ligands.

Conotoxin peptides can also be administered in a cell based delivery system in which a DNA sequence encoding the conotoxin peptide is introduced into cells designed for implantation in the body of the subject. In particular embodiments, this delivery method can be used in the spinal cord region. Suitable delivery systems are described in U.S. Pat. No. 5,550,050 and published PCT Application Nos. WO92/19195, WO94/25503, WO 95/01203, WO95/05452, WO96/02286, WO96/02646, WO96/40871, WO96/40959, and WO97/12635.

Suitable DNA sequences can be prepared synthetically for each conotoxin peptide on the basis of the disclosed sequences and the known genetic code. Briefly, the term "gene" refers to a nucleic acid sequence that encodes a conotoxin peptide. This definition includes various sequence polymorphisms, mutations, and/or sequence variants wherein such alterations do not affect the function of the encoded conotoxin peptide. The term "gene" may include not only coding sequences but also regulatory regions such as promoters, enhancers, and termination regions. The term further can include all introns and other DNA sequences spliced from the mRNA transcript, along with variants resulting from alternative splice sites. Nucleic acid sequences encoding the conotoxin peptide can be DNA or RNA that directs the expression of the conotoxin peptide. These nucleic acid sequences may be a DNA strand sequence that is transcribed into RNA or an RNA sequence that is translated into protein. The nucleic acid sequences include both the full-length nucleic acid sequences as well as non-full-length sequences derived from the full-length protein. The sequences can also include degenerate codons of the native sequence or sequences that may be introduced to provide codon preference in a specific cell type. Gene sequences to encode conotoxin peptide disclosed herein are available in publicly available databases and publications.

In some embodiments, the polynucleotide includes a plasmid, a cDNA, or an mRNA that can include, e.g., a sequence (e.g., a gene) for expressing a conotoxin peptide. Suitable plasmids include standard plasmid vectors and minicircle plasmids that can be used to transfer a gene to a cell. The polynucleotides (e.g., minicircle plasmids) can further include any additional sequence information to facilitate transfer of the genetic material (e.g., a sequence encoding a conotoxin peptide) to a cell. For example, the polynucleotides can include promoters, such as general promoters, tissue-specific promoters, cell-specific promoters, and/or promoters specific for the nucleus or cytoplasm. Promoters and plasmids (e.g., minicircle plasmids) are generally well known in the art and can be prepared using conventional techniques. As described further herein, the polynucleotides can be used to transfect cells. Unless otherwise specified, the terms transfect, transfected, or transfecting can be used to indicate the presence of exogenous polynucleotides or the expressed polypeptide therefrom in a cell. A number of vectors are known to be capable of mediating transfer of genes to cells, as is known in the art.

B. Methods of Identifying Drug Candidates

Conotoxin peptides disclosed herein are also useful in methods of identifying drug candidates for use in treating conditions associated with the α9α10 subtype of the nAChR. These methods include screening a drug candidate for its ability to block the activity of the α9α10 subtype of the nAChR.

"Drug candidate" refers to any peptide, protein (including antibodies or antibody fragments) or compound (small molecule or otherwise) that may block or otherwise interfere with the activity of a target (i.e., the α9α10 subtype). Small molecules may belong to any chemical class suspected to interact with a protein complex and expected to be pharmaceutically acceptable. Drug candidates can be found in nature, synthesized by combinatorial chemistry approaches, and/or created via rational drug design.

Blocking can be measured as described elsewhere herein except that the drug candidate can be compared to conotoxin peptides disclosed herein rather than or in addition to RgIA. Conotoxin peptides are useful in methods of identifying drug candidates that mimic the therapeutic activity of the conotoxin peptide. Such methods include the steps of: (a) conducting a biological assay on a drug candidate to determine its therapeutic activity; and (b) comparing the results obtained from the biological assay of the drug candidate to the results obtained from the biological assay of a conotoxin peptides disclosed herein.

Drug candidates may also interfere with the activity of the α9α10 subtype through interaction with polynucleotides (e.g., DNA and/or RNA), and/or enzymes. Such drug candidates can be known or potential DNA modifying agents, including DNA damaging agents (e.g., intercalating agents that interfere with the structure of nucleic acids); DNA bending agents; mismatch binding proteins; and/or alkylating agents.

One goal of rational drug design is to identify drug candidates which are, for example, more active or stable forms of the conotoxin peptide, or which, e.g., enhance or interfere with the function of a peptide in vivo. Several approaches for use in rational drug design include analysis of three-dimensional structure, alanine scans, molecular modeling and use of anti-id antibodies. Such techniques may include providing atomic coordinates defining a three-dimensional structure of a protein complex formed by the conotoxin peptide and the α9α10 subtype of the nAChR, and designing or selecting drug candidates capable of interfering with the interaction between a conotoxin peptide and the α9α10 subtype of the nAChR based on said atomic coordinates.

The designing of drug candidates that mimic or improve the effects of a conotoxin peptide is a known approach to the development of pharmaceuticals based on a "lead" conotoxin peptide. This approach might be desirable where a particular conotoxin peptide is difficult or expensive to synthesize or where it is unsuitable for a particular method of administration, e.g., the use of pure peptides as active agents for oral compositions can be challenging as they tend to be quickly degraded by proteases in the alimentary canal. Mimetic design, synthesis, and testing are also used to avoid randomly screening large numbers of molecules for a target property.

Once a drug candidate is selected for further study or development, its structure can be modeled according to its physical properties, e.g., stereochemistry, bonding, size, and/or charge, using data from a range of sources, e.g., spectroscopic techniques, x-ray diffraction data, and NMR. Computational analysis, similarity mapping (which models the charge and/or volume of a drug candidate, rather than the bonding between atoms), and other techniques can be used in this modeling process.

When a drug candidate is selected, attachment of further chemical groups can be evaluated. Chemical groups can be selected so that the drug candidate is easy to synthesize, is likely to be pharmacologically acceptable, and does not degrade in vivo, while, in some embodiments, retaining or improving the biological activity of a lead conotoxin peptide. Alternatively, where the drug candidate is peptide-based, further stability can be achieved by cyclizing the peptide, which increases its rigidity. The drug candidates with attached chemical groups can be further screened to see ensure they retain target properties. Further optimization or modification can then be carried out to arrive at one or more final drug candidates for in vivo or clinical testing.

Following selection and optimization of a drug candidate, the selected and optimized drug candidate may be manufactured and/or used in a pharmaceutical composition for administration to subjects.

III. Pharmaceutical Compositions

Conotoxin peptides can be formulated within pharmaceutical compositions. "Pharmaceutical compositions" mean physically discrete coherent units suitable for medical administration. "Pharmaceutical composition in dosage unit form" means physically discrete coherent units suitable for medical administration, each containing a therapeutically effective amount, or a multiple (up to four times) or sub-multiple (down to a fortieth) of a therapeutically effective amount of a conotoxin peptide with a pharmaceutically acceptable carrier. Whether the pharmaceutical composition contains a daily dose, or for example, a half, a third or a quarter of a daily dose, will depend on whether the pharmaceutical composition is to be administered once or, for example, twice, three times or four times a day, respectively.

The amount and concentration of a conotoxin peptide in a pharmaceutical composition, as well as the quantity of the pharmaceutical composition can be selected based on clinically relevant factors, the solubility of the conotoxin peptide in the pharmaceutical composition, the potency and activity of the conotoxin peptide, and the manner of administration of the pharmaceutical composition. It is only necessary that the conotoxin peptide constitute a therapeutically effective amount, i.e., such that a suitable effective dosage will be consistent with the dosage form employed in single or multiple unit doses.

The pharmaceutical compositions will generally contain from 0.0001 to 99 wt. %, preferably 0.001 to 50 wt. %, more preferably 0.01 to 10 wt. % of the conotoxin peptide by weight of the total composition. In addition to the conotoxin peptide, the pharmaceutical compositions can also contain other drugs or agents. Examples of other drugs or agents include analgesic agents, cytokines, and therapeutic agents in all of the major areas of clinical medicine. When used with other drugs or agents, the conotoxin peptides may be delivered in the form of drug cocktails. A cocktail is a mixture of any one of the conotoxin peptides with another drug or agent. In this embodiment, a common administration vehicle (e.g., pill, tablet, implant, pump, injectable solution, etc.) would contain both the conotoxin peptide in combination with the other drugs or agents. The individual components of the cocktail can each be administered in therapeutically effective amounts or their administration in combination can create a therapeutically effective amount.

Pharmaceutical compositions include pharmaceutically acceptable carriers including those that do not produce significantly adverse, allergic, or other untoward reactions that outweigh the benefit of administration, whether for research, prophylactic, and/or therapeutic treatments. Exemplary pharmaceutically acceptable carriers and formulations are disclosed in Remington, 2005. Moreover, pharmaceutical compositions can be prepared to meet sterility, pyrogenicity, and/or general safety and purity standards as required by U.S. Food and Drug Administration (FDA) Office of Biological Standards and/or other relevant foreign regulatory agencies.

Typically, a conotoxin peptide will be admixed with one or more pharmaceutically acceptable carriers chosen for the selected mode of administration. For examples of delivery methods see U.S. Pat. No. 5,844,077.

Exemplary generally used pharmaceutically acceptable carriers include any and all bulking agents, fillers, solvents, co-solvents, dispersion media, coatings, surfactants, antioxidants, preservatives, isotonic agents, releasing agents, absorption delaying agents, salts, stabilizers, buffering agents, chelating agents, gels, binders, disintegration agents, wetting agents, emulsifiers, lubricants, coloring agents, flavoring agents, sweetening agents and perfuming agents.

Exemplary buffering agents include citrate buffers, succinate buffers, tartrate buffers, fumarate buffers, gluconate buffers, oxalate buffers, lactate buffers, acetate buffers, phosphate buffers, histidine buffers, and trimethylamine salts.

Exemplary preservatives include phenol, benzyl alcohol, meta-cresol, methyl paraben, propyl paraben, octadecyldimethylbenzyl ammonium chloride, benzalkonium halides, hexamethonium chloride, alkyl parabens, methyl paraben, propyl paraben, catechol, resorcinol, cyclohexanol, and 3-pentanol.

Exemplary isotonic agents include polyhydric sugar alcohols, trihydric sugar alcohols, or higher sugar alcohols, such as glycerin, erythritol, arabitol, xylitol, sorbitol, and mannitol.

Exemplary stabilizers include organic sugars, polyhydric sugar alcohols, polyethylene glycol, sulfur-containing reducing agents, amino acids, low molecular weight polypeptides, proteins, immunoglobulins, hydrophilic polymers, and polysaccharides.

Exemplary antioxidants include ascorbic acid, methionine, vitamin E, cysteine hydrochloride, sodium bisulfite, sodium metabisulfite, sodium sulfite, oil soluble antioxidants, ascorbyl palmitate, butylated hydroxyanisole (BHA), butylated hydroxytoluene (BHT), lecithin, propyl gallate, aloha-tocopherol, metal chelating agents, citric acid, ethylenediamine tetraacetic acid (EDTA), sorbitol, tartaric acid and phosphoric acid.

Exemplary lubricants include sodium lauryl sulfate and magnesium stearate.

Exemplary pharmaceutically acceptable salts include acidic and/or basic salts, formed with inorganic or organic acids and/or bases, preferably basic salts. While pharmaceutically acceptable salts are preferred, particularly when employing the conotoxin peptides as medicaments, other salts find utility, for example, in processing these conotoxin peptides, or where non-medicament-type uses are contemplated. Salts of these conotoxin peptides may be prepared by techniques recognized in the art.

Exemplary pharmaceutically acceptable salts include inorganic and organic addition salts, such as hydrochloride, sulphates, nitrates, phosphates, acetates, trifluoroacetates, propionates, succinates, benzoates, citrates, tartrates, fumarates, maleates, methane-sulfonates, isothionates, theophylline acetates, and salicylates. Lower alkyl quaternary ammonium salts can also be used.

For oral administration, the conotoxin peptides can be formulated into solid or liquid preparations such as capsules, pills, tablets, lozenges, melts, powders, suspensions, or emulsions. In preparing the compositions in oral dosage form, any of the usual pharmaceutically acceptable carriers may be employed, such as, for example, carriers such as starches, sugars, diluents, granulating agents, lubricants, binders, disintegrating agents, and the like in the case of oral solid preparations (such as, for example, powders, capsules and tablets); or water, glycols, oils, alcohols, flavoring agents, preservatives, coloring agents, suspending agents, and the like in the case of oral liquid preparations (such as, for example, suspensions, elixirs and solutions). Because of their ease in administration, tablets and capsules can represent an advantageous oral dosage unit form, in which case solid pharmaceutical carriers are obviously employed. If desired, tablets may be sugar-coated or enteric-coated by standard techniques. The conotoxin peptide can be encapsulated to make it stable to passage through the gastrointestinal tract while at the same time, in certain embodiments, allowing for passage across the blood brain barrier. See for example, WO96/11698.

For parenteral administration, the conotoxin peptides may be dissolved in a pharmaceutically acceptable carrier and administered as either a solution or a suspension. Exemplary pharmaceutically acceptable carriers include water, saline, dextrose solutions, fructose solutions, ethanol, or oils of animal, vegetative, or synthetic origin. The carrier may also contain other ingredients, for example, preservatives, suspending agents, solubilizing agents, buffers, and the like.

The conotoxin peptides can be in powder form for reconstitution in the appropriate pharmaceutically acceptable carrier at the time of delivery. In another embodiment, the unit dosage form of the conotoxin peptide can be a solution of the conotoxin peptide, or a pharmaceutically acceptable salt thereof, in a suitable diluent in sterile, hermetically sealed ampoules or sterile syringes.

Conotoxin peptides can also be formulated as depot preparations. Depot preparations can be formulated with suitable polymeric or hydrophobic materials (for example as an emulsion in an acceptable oil) or ion exchange resins, or as sparingly soluble derivatives, for example, as a sparingly soluble salts.

Additionally, conotoxin peptides can be formulated as sustained-release systems utilizing semipermeable matrices of solid polymers containing at least one compound. Various sustained-release materials have been established and are well known by those of ordinary skill in the art. Sustained-release systems may, depending on their chemical nature, release conotoxin peptides following administration for a few weeks up to over 100 days.

Administration of the conotoxin peptide can also be achieved using pumps (see, e.g., Luer et al., (1993), Zimm, et al., (1984) and Ettinger, et al., (1978)); microencapsulation (see, e.g., U.S. Pat. Nos. 4,352,883, 4,353,888, and 5,084,350); continuous release polymer implants (see, e.g., U.S. Pat. No. 4,883,666); and macroencapsulation (see, e.g., U.S. Pat. Nos. 5,284,761, 5,158,881, 4,976,859, and 4,968,733 and published PCT patent applications WO92/19195, WO 95/05452);

When the conotoxin peptides are administered intrathecally, they may also be dissolved in cerebrospinal fluid. Naked or unencapsulated cell grafts to the CNS can also be used. See, e.g., U.S. Pat. Nos. 5,082,670 and 5,618,531.

EXEMPLARY EMBODIMENTS

1. A conotoxin peptide including the formula of SEQ ID NO:22, SEQ ID NO: 30, SEQ ID NO:31, SEQ ID NO:32. SEQ ID NO:33, SEQ ID NO:34, SEQ ID NO:35, SEQ ID NO:36 or SEQ ID NO:37.

2. A conotoxin peptide of embodiment 1, including the formula of SEQ ID NO:2, SEQ ID NO:23, SEQ ID NO:24, SEQ ID NO:25, SEQ ID NO:26, SEQ ID NO:27, SEQ ID NO:28 or SEQ ID NO:29.

3. A conotoxin peptide of embodiments 1 or 2 including the formula of: SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, or SEQ ID NO:21.

4. A conotoxin peptide of any one of embodiments 1-3, wherein the C-terminus of the conotoxin peptide is a carboxylic acid group.

5. A conotoxin peptide of 4, wherein a Tyr, iodo-Tyr, or a fluorescent tag is added to the carboxylic acid group.

6. A conotoxin peptide of any one of embodiments 1-5 having a Tyr, iodo-Tyr, pyroglutamate or fluorescent tag added to the N-terminus of the conotoxin peptide.

7. A conotoxin peptide of any one of embodiments 1-6, wherein the conotoxin peptide includes an amide cyclized backbone.

8. A pharmaceutical composition including a conotoxin peptide of any one of embodiments 1-7 or a salt thereof and a pharmaceutically acceptable carrier.

9. A method for treating at least one condition associated with the α9α10 subtype of the nicotinic acetylcholine receptor (nAChR) in a subject in need thereof including administering to the subject a therapeutically effective amount of a conotoxin peptide of embodiments 1-7 or a pharmaceutical composition of embodiment 8, thereby treating the condition.

10. A method of embodiment 9 wherein the at least one condition is pain.

11. A method of embodiment 10 wherein the pain is general pain, chronic pain, neuropathic pain, nociceptive pain, inflammatory pain, pain related to and/or induced by peripheral nerve or nociceptor damage, pain related to and/or induced by inflammatory disorders, pain related to and/or induced by metabolic disorders, pain related to and/or induced by virus infection, pain related to and/or induced by cancers, pain related to and/or induced by chemotherapeutic agents, pain related to and/or induced after surgical procedure, and/or pain related to and/or induced by burn and/or other physical tissue injury.

12. A method of any one of embodiments 10, wherein the pain is chemotherapy-induced neuropathic pain.

13. A method of any one of embodiments 10, wherein the pain is chronic pain and/or neuropathy related to burn or other thermal tissue injury.

14. A method of embodiments 10, wherein the pain is pain and/or neuropathy induced after surgery or other physical tissue injury.

15. A method of embodiment 9 wherein the at least one condition is an inflammatory condition.

16. A method of embodiment 15 wherein the inflammatory condition is inflammation, chronic inflammation, a rheumatic disease, sepsis, fibromyalgia, inflammatory bowel disease, sarcoidosis, endometriosis, uterine fibroids, an inflammatory skin disease, an inflammatory condition of the lungs, a disease associated with inflammation of the nervous system, periodontal disease, and/or cardiovascular disease.

17. A method of embodiment 16 wherein the rheumatic disease is one or more of arthritis, lupus, ankylosing spondylitis, fibromyalgia, tendonitis, bursitis, scleroderma, or gout.

18. A method of embodiment 16 wherein the inflammatory bowel disease is ulcerative colitis or Crohn's disease.

19. A method of embodiment 16 wherein the inflammatory skin disease is psoriasis or impaired wound healing.

20. A method of embodiment 16 wherein the inflammatory condition of the lungs is asthma or chronic obstructive pulmonary disease.

21. A method of embodiment 16 wherein the inflammation of the nervous system is Parkinson's disease or Alzheimer's disease.

22. A method of embodiment 9 wherein the at least one condition is pain and inflammation.

23. A method of any one of embodiments 9, and 15-21 wherein the at least one condition is inflammation and neuropathy.

24. A method of any one of embodiments 15-20, wherein the inflammation is mediated by immune cells.

25. A method of any one of embodiments 9 and 15-21 wherein the at least one condition is long-term inflammation and peripheral neuropathy following injury.

26. A method of embodiment 9 wherein the at least one condition is cancer related chronic pain and neuropathy.

27. A method of embodiment 9 wherein the at least one condition is cancer.

28. A method of embodiment 27 wherein the cancer is breast cancer.

29. A method of embodiments 10 or 11 wherein the pain is chemotherapy-related chronic pain and/or chemotherapy-related neuropathy.

The Examples below are included to demonstrate particular embodiments. Those of ordinary skill in the art should recognize in light of the present disclosure that many changes can be made to the specific embodiments disclosed herein and still obtain a like or similar result without departing from the spirit and scope of the disclosure.

EXAMPLES

Example 1. Preclinical Optimization of RgIA

Lead analog conotoxin peptides are evaluated in in vitro characterization studies and animal pain models in order to select lead conotoxin peptides for preclinical development.

TABLE 1

| Peptides | | |
|---|---|---|
| Analog No. | SEQ ID NO. | Sequence |
|  | 1 | GCCSDPRCRYRCR |
| 2 | 19 | GCCTDPRCX2X3QCR |
| 3 | 3 | GCCTDPRCX2X3QCY |
| 4 | 4 | GCCTDPRCX2X3QCRRR |
| 5 | 5 | GCCTDPRCX2X3QCYRR |
| 6 | 6 | GCCTDPRCX2X3QCRRY |
| 7 | 7 | GCCTDPRCX2X3QCF |
| 8 | 8 | GCCTDPRCX2X3QCW |
| 9 | 9 | GCCTDPRCX2X3QCYY |
| 10 | 10 | GCCTDPRCX2X3QCYR |
| 11 | 11 | GCCTDPRCRX3QCY |

TABLE 1 -continued

Peptides

| Analog No. | SEQ ID NO. | Sequence |
|---|---|---|
| 12 | 12 | GCCTDPRCRX3QCRRR |
| 13 | 13 | GCCTDPRCRX3QCYRR |
| 14 | 14 | GCCTDPRCRX3QCRRY |
| 1 | 15 | GCCTDPRCRX3QCF |
| 16 | 16 | GCCTDPRCRX3QCW |
| 17 | 17 | GCCTDPRCRX3QCYY |
| 18 | 18 | GCCTDPRCRX3QCYR |
|  | 20 | GX4X4TDPRCX2X3QCR |
|  | 21 | GCCSDPRCRX3RCR |

X2 = Citrulline
X3 = mono-iodo-Tyrosine
X4 = Selenocysteine

TABLE 2

Activity of Peptides

| Analog No. | SEQ ID NO. | Human α9α10 $IC_{50}$ (nM) | Human α9α10 flowing 95% confidence interval (nM) | Fold improvement |
|---|---|---|---|---|
| 1 | 1 | 494 |  | 1 |
|  | 21 | 107 |  | 4.6 |
|  | 20 | 87 |  | 5.7 |
| 2 | 19 | 5.72 | 4.63 to 7.07 | 86 |
| 3 | 3 | 0.808 | 0.416 to 1.57 | 611 |
| 4 | 4 | 4.55 | 3.30 to 6.29 | 109 |
| 5 | 5 | 1.52 | 1.32 to 1.75 | 325 |
| 6 | 6 | 4.11 | 3.52 to 4.79 | 120 |
| 7 | 7 | 1.05 | 0.662 to 1.67 | 470 |
| 8 | 8 | 2.09 | 1.68 to 2.59 | 236 |
| 9 | 9 | 0.893 | 0.613 to 1.30 | 553 |
| 10 | 10 | 0.826 | 0.659 to 1.04 | 598 |
| 11 | 11 | 0.44 | 0.35 to 0.54 | 1,123 |

Sel = Selenocysteine
$IC_{50}$ hα9α10: $IC_{50}$ (in nM) on human α9α10 nAChR expressed in *Xenopus* oocytes.
The $IC_{50}$ values in Table 2 were calculated using Analogs X-Y with a C-terminal COOH Parent peptide, RgIA, has $IC_{50}$ of 494 nM on human α9α10 nAChR (Azam et al., 2012). Thus, these analog conotoxin peptides are 80-1100 fold more potent than parent peptide on human α9α10 nAChR.

Example 2. Analysis of nAChR Subtype Specificity and Potency

Analog conotoxin peptides are tested for functional activity on cloned nAChRs heterologously expressed in *Xenopus laevis* oocytes. The methods to accomplish this have been routinely employed (McIntosh et al., 2005). The oocyte system has the advantage of providing immediate information regarding antagonist vs. agonist activity and can detect analog conotoxin peptides acting by allosteric mechanisms. Compounds with activity on α9α10 receptors will be counter-screened against α7 and α1β1δε nAChRs, the two subtypes most closely related to α9α10. Analog conotoxin peptides that are selected for further development will demonstrate an $IC_{50} \leq 100$ nM and an $I_{max} \geq 80\%$ for the α9α10 receptor and ≥200-fold selectivity for α9α10 over either α7 or α1β1δε. Analog conotoxin peptides not meeting these criteria will be discarded without further evaluation, and the remaining analogs will be tested in detail against all expressible pair-wise and homomeric combinations of nAChR subunits to determine their subtype specificity. Dose-response curves and kinetic constants (both association and dissociation) will be obtained for each subtype combination. Because the use of oocytes represents a functional assay, other more subtle features of the analog conotoxin peptides can also be assessed, such as their effects on reversal potential and the voltage dependence of their block.

Figure 2:
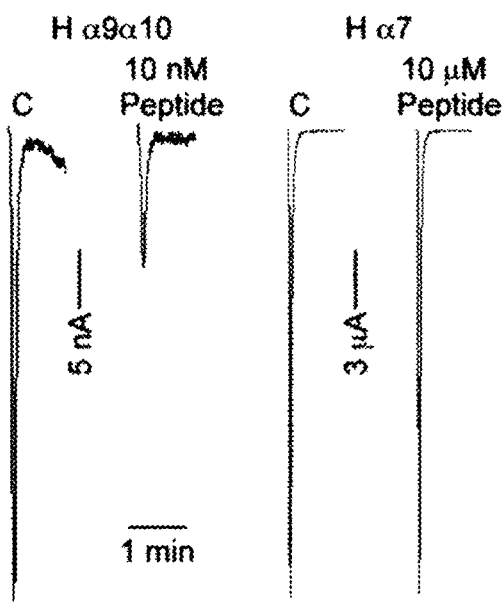
Figure 3:
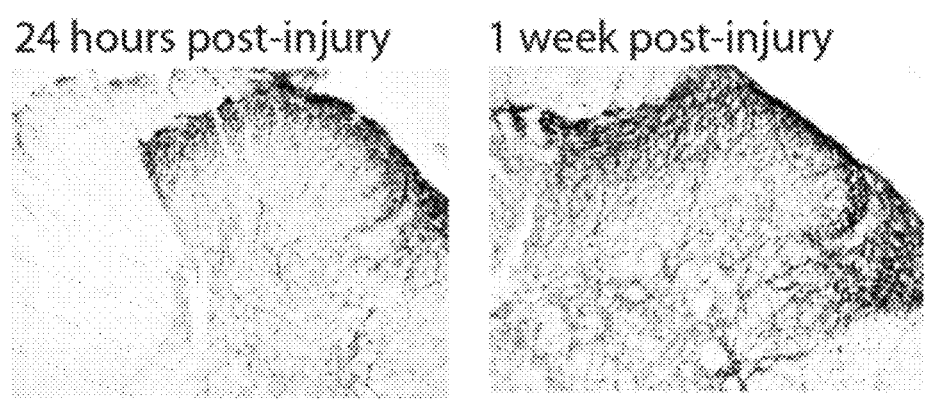

Analog 2 (SEQ ID NO:4) has already demonstrated acceptable potency and selectivity. This analog conotoxin peptide has potent antagonist activity (~8 nM $IC_{50}$, FIG. 2) on α9α10 nAChRs, while its $IC_{50}$ on all other subtypes is greater than 10 μM (n=3-5). Thus, Analog 2 (SEQ ID NO:4) discriminates with a 1000-fold difference in its $IC_{50}$ the α9α10 nAChRs versus other major subtypes including muscle nAChR (α1β1γδ) and neuronal nAChRs (α2β2, α2β4, α3β2, α3β4, α4β2, α4β4, αδ/α3β2, α6β4, and α7).

The lead analog conotoxin peptides are tested on other receptor subtypes including the structurally related 5-HT3 and GABAA receptors. More general analgesia-related targets, including opioid, GABAB, muscarinic and norepinephrine transporters and receptors are also examined.

Example 3. Production of a Cell Line Stably Expressing α9α10n AChRs

Cell lines that stably express a variety of subtypes of nAChRs have previously been created. However, a cell line stably expressing the more recently identified α9α10 subtype has not yet been developed. Human embryonic kidney (HEK) cells that do not naturally express nAChRs have been successfully used to express a number of nAChR subtypes (Capelli, et al., 2011; Abdrakhmanova, et al., 2010; Xiao, et al., 2009; Kracun, et al., 2008; Xiao, et al., 1998). These cells are advantageous in that they do not naturally express nAChRs. HEK293 cells are used to construct stable clones that express α9α10 nAChRs. The primary expression construct contains the coding sequences of α9 and α10 separated by the encephalomyocarditis virus internal ribosome entry sequence (IRES). The mixture of RNAs, (5'UTR (untranslated region) of RNA4 of alfalfa mosaic virus-α9 coding sequence-partial 3'UTR sequence of α9) and (5'UTR of RNA4 of alfalfa mosaic virus-α10 coding sequence-partial 3'UTR sequence of α10) has been observed to result in high expression of α9α10 receptors in *Xenopus* oocytes following transient transfection. These two expression cassettes are cloned into the pIRES vector downstream of the cytomegalovirus promoter, and the selectable marker is replaced with the (green fluorescent protein (GFP):zeocin gene (Bennett, et al., 1998), allowing for the identification of clones by both GFP fluorescence and zeocin-based selection.

HEK293 cells are transfected with DNA from the expression vector using a reagent such as FuGENE® HD transfection reagent (Roche Applied Science). Florescence activated cell sorting (FACS) is used to identify GFP expressing clones and a fluorescence microscopy-based intracellular calcium assay is used to identify clones that express functional α9α10 receptors (Capelli, et al., 2011; Kracun, et al., 2008; Teichert, et al., 2012). Forty-eight hours after transfection, GFP-expressing cells are isolated by FACS and plated in complete media. Twenty-four hours after plating, a portion of the cells (~50,000) is replated on poly-L-lysine coated 24-well plates for calcium imaging studies. Calcium imaging is undertaken by exposing the cells to the calcium sensitive fluorescent dye Fluo-4-acetoxy methyl ester (Fura-2-AM, Invitrogen). Fura-2-AM enters the cell and undergoes a change in excitation spectrum upon binding to calcium (Barreto-Chang and Dolmetsch, 2009). Because intracellular calcium levels rise in proportion to α9α10 receptor expression, this analysis can identify highly-expressing clones. Standard ratiometric imaging video microscopy for Fura-2-AM will be employed. The effect of agonists and antagonists on fluorescence emission will be monitored. Untransfected cells will be used as a negative control and an established α3β4 nAChR cell line will be used as a positive control. Clones that stably express the receptor will be grown under selection and cryopreserved according to standard methods. The final cell line(s) will be assayed using patch clamp electrophysiology to confirm the pharmacology and function of expressed receptors.

Alternative systems used to generate a cell line that adequately expresses the α9α10 subtype include: (1) cloning of the endogenous 5'- and 3'-UTRs from the α9 and α10 genes into the bi-directional vector, pBi (Clontech) to obtain: (5'α9UTR-α9 coding sequence-3'α9UTR)-bi-directional promoter-(5'α10UTR-α10 coding sequence-3'α10UTR), and replacement of the selectable marker with GFP:zeocin as previously described; and (2) insertion of cDNA encoding α9α10 with their endogenous UTRs into pTRE3G-hyg vector (a tet-inducible bidirectional vector) and replacement of the selection marker with GFP:Zeocin in order to produce a tetracycline-inducible system for expression. For alternative system #2, HEK293 Tet-On® cells (Clontech) are transfected and gene expression will be initiated by adding doxycycline to the media.

Example 4. In Vivo Pain Models to Assess Potency of Conotoxin Peptides

Full thickness thermal injury model: Sprague Dawley rats are anesthetized prior to thermal injury with 4% isofluorane in oxygen. Injury is induced using a temperature-controlled super soldering station equipped with a slanted soldering tip (RX-80HRT-5.4D) (coot, Hiroshima, Japan). This procedure results in a full-thickness thermal injury. Skin histology using hematoxylin and eosin has confirmed the depth and repeatability of this injury. To prevent infection, silver sulfadiazine (1%) ointment is applied to the injured or uninjured site on the hind paw once daily until scar tissue forms on the injured animals (7 days after injury). To examine the efficacy and potency of conotoxin peptides on thermal injury-evoked pain, mechanical allodynia and thermal hyperalgesia are analyzed for up to 21 days following injury.

Spinal nerve ligation model (SNL): SNL involves partial deafferentation via ligature of the L5 spinal nerve, leaving other nearby nerves intact and allowing for behavioral testing on the rat hindpaw. During degeneration of the affected nerves, the nearby spared nerves are exposed to an environment of chemical inflammatory mediators similar to that seen in traumatic injury in the clinic. The SNL model is a widely accepted model of experimental neuropathic pain, reliably producing both thermal hyperalgesia and mechanical allodynia within 1-2 days of ligation with low variability and without motor coordination deficits (Kim et al., 1992).

Anesthesia is induced in Sprague Dawley rats with 4% isofluorane in oxygen and subsequently maintained with ~2-2.5% isofluorane delivered through a nose cone. The hair on the rats is clipped and the surgical site disinfected with reciprocal treatments of 2% betadine and 70% ethanol in water. The surgery is performed with the aid of a dissecting microscope. A ~2 cm longitudinal incision is made 0.8 cm lateral from the midline of the animal. The incision exposes the paraspinal muscles which, together with adjacent connective tissue, are removed from the level of the L5 spinal process to the sacrum. The L6 transverse process is removed very close to the vertebrae, allowing access to the L4 and L5 spinal nerves. A 6-0 silk thread is placed under the L5 nerve, and the nerve is tightly ligated. For sham animals, the thread is placed under the L5 nerve but is removed without ligation. In the absence of noticeable bleeding, the wound is closed in layers. The fascia is sutured using 3-0 silk thread, and metal wound clips are used to close the skin. Anesthesia is discontinued and the animals are returned to their cages. Two subcutaneous injections of 0.05 mg/kg buprenorphine are given; one immediately following the surgery and one 8 hours after surgery. This analgesia is required due to the invasiveness of the surgery and does not impact subsequent measures of analgesic activity of the conotoxin peptides. Animals with obvious motor deficits following surgery are euthanized and excluded from behavioral studies.

Mechanical allodynia test: Injured rats that develop mechanical allodynia, which is pain that results from a stimulus that would not normally cause pain, are identified by using an electronic von Frey esthesiometer (Pitcher, et al., 1999). Rats are acclimated to the test chamber for twenty minutes prior to the start of the procedure. The device delivers pressure to the midplantar region of the hind paw for up to 15 seconds (2 g/s increases). The upper threshold for the tests is 30 grams. The pressure at which the injured rat removes its paw from the stimulus (the withdrawal threshold) is compared to the pressure at which it removed its paw prior to injury (the baseline threshold). The effect of conotoxin peptide treatment on the withdrawal threshold is then evaluated. Sham-operated and vehicle-treated animals serve as controls. Measurements are taken in triplicate for each animal at each time point.

Thermal hyperalgesia testing: Thermal hyperalgesia is an exaggerated response to painful heat or cold, which sometimes results from an injury. The animals' response to heat is tested to determine if treatment with the conotoxin peptides alleviates this hyperalgesia. Animals are tested before injury, as with the mechanical allodynia test, to establish baseline responses. To determine the heat-withdrawal threshold, the plantar test (Hargreaves method) is used (Hargreaves, et al., 1988). Animals are placed in an acrylic enclosure positioned on top of an elevated, temperature-controlled glass plate. A radiant heat source (visible light) is focused on the plantar surface of the hind paw, and thermal thresholds are identified as the time until paw withdrawal from the heat source.

Immunohistochemistry studies: Immunohistochemical analyses on tissues obtained from subjects in each of the test groups is performed to determine if test conotoxin peptides affect the activation and/or expression of molecular mediators of nociception. The obtained tissue includes the dorsal horn of the spinal cord, as well as other nervous system components. Antibodies raised against p38 MAPK, phosphorylated p38 MAPK, OX-42, c-Fos, calcitonin gene-related peptide (CGRP), Substance P, mu opioid receptor, neuronal nuclei and other molecules as needed are used in these analyses. To obtain tissue, the rats are anesthetized with sodium pentobarbital and then euthanized by exsanguination-perfusion with 4% paraformaldehyde. Tissues are post-fixed in 4% paraformaldehyde for 24 hours and then stored in 30% sucrose until sectioning. Tissues are frozen-sectioned at 30 μm on a cryostat directly onto treated slides.

Slides are washed with PBS and incubated with specific primary antibodies to label the molecule of interest. Fluorescently-labeled or biotin-conjugated secondary antibodies are used as detection reagents and the resulting slides are visualized by fluorescent or brightfield microscopy.

Analog screening for drug efficacy in rodent pain models: In an initial screening experiment, analogs are evaluated in the SNL and FTB pain models using daily subcutaneous doses of 33 µg/kg. This dose is consistent with the approximate half-maximal dose from previous RgIA experiments and is anticipated to yield a maximum serum concentration of approximately the $IC_{50}$ of each analog on the $\alpha 9\alpha 10$ receptor. Conotoxin peptides or vehicle control treatment begins on the day of injury and continue for 21 days. Animals are assessed on days 7, 14, and 21. Testing is performed immediately preceding dose administration (24 hours after the last dose) and 30 minutes following dose administration on testing days. Study end points include the mechanical and thermal withdrawal thresholds, daily clinical observations, and weekly bodyweights. This initial study can be used to select the two most effective analogs for dose-response studies.

Effect of conotoxin peptides on pronociceptive peptide release from the spinal cord: Thermal injury and spinal nerve ligation evoke enhanced proinflammatory peptide release, including CGRP and substance P, in the sensory dorsal horn of the spinal cord (FIG. 3). If the conotoxin peptides are effective analgesics for pain following thermal injury, then a corresponding reduction in the expression of CGRP and substance P should be observed in the spinal cord as a measure of reduced pain signaling. In order to test this hypothesis, rats undergo thermal injury of the right hindpaw, and daily subcutaneous administration of conotoxin peptide or vehicle begins 24 hours thereafter. Groups of animals (n=5/group) are sacrificed at 24 hours, 1 week, and 2 weeks and their tissues are fixed by perfusion-fixation. Recovered tissues are frozen and sectioned onto slides. Slides are rinsed in buffer, incubated for 24 hours with a primary antibody against CGRP (1:10,000; Immunostar) or substance P (1:50,000; Immunostar) and developed with an appropriate secondary antibody and nickel-enhanced diaminobenzidine.

Using the same rats from this study, the effect of RgIA treatment on burn pathology and wound healing is also evaluated. Fixed hindpaws are collected and sectioned for both H&E staining and fluorescent immunohistochemistry to compare RgIA-treated vs. vehicle-treated rats. Fluorescent immunohistochemistry is used to detect changes in nerve fiber innervation, expression of various inflammatory mediators, molecular determinants of scar formation, markers of cell proliferation, and proteins involved in matrix remodeling.

Example 5. Efficacy in Chemotherapy Induced Neuropathic Pain

The effect of RgIA administration on peripheral pain elicited by oxaliplatin (OXA), a commonly used platinum salt chemotherapeutic, was evaluated using an established in vivo model of chemotherapy-induced neuropathic pain (CINP). OXA CINP in rodents is a highly relevant and widely used model of neuropathic pain (NPP) (Authier et al., 2009). Rats chronically treated with OXA developed peripheral NPP including mechanical hyperalgesia, mechanical allodynia, and thermal allodynia (FIGS. 4A-4J). In this model, daily administration of RgIA had significant analgesic effects on days 14 and 21 (FIGS. 4A, 4B, 4E, 4F, and 4I). These data serve as proof of concept that RgIA can prevent chemotherapy-induced peripheral NPP. The same model is used to evaluate the in vivo analgesic potential of conotoxin peptides. FIGS. 4C, 4D, 4G, 4H, and 4J show data demonstrating an analgesic effect of Analog 3 (also referred to as CSP-4; SEQ ID NO:3) in this preventive treatment paradigm.

RgIA and conotoxin peptides can be tested in both a preventive treatment paradigm and in a therapeutic treatment paradigm of the OXA CINP model. In both paradigms, a minimum effective dose will be determined through dose response studies in which a minimum of three-five treatment doses are tested. In additional studies, conotoxin peptides are tested and compared for efficacy when administered at a low effective dose.

In the OXA-induced CINP model, male Sprague-Dawley rats (~250 g) are treated with 2.4 mg/kg OXA, administered intraperitoneally (i.p.) for 5 consecutive days every week for 3 weeks (15 injections). OXA is dissolved in a 5% glucose-water solution. RgIA and conotoxin peptides, positive control drugs, or negative control vehicle, are administered intramuscularly (i.m.) or subcutaneously (s.c.) daily starting on the indicated day for a given experiment (Bennet, 2003). Examples of positive control drugs include gabapentin/pregabalin and morphine. For treatment in the preventive modality, rats receive RgIA or conotoxin peptide for 21 days starting the day before OXA injection. For the therapeutic treatment, drug administration begins after the onset of NPP, which is typically 14 days for OXA CINP.

Mechanical hyperalgesia is measured by the Randall-Selitto test (Di Cesare, 2012). Mechanical allodynia by the von Frey test and up/down method as described by Chaplan, et al., 1994 can be used. Cold-allodynia is measured using the cold plate test as described below. Measurements for all tests are taken on days 0 (baseline), 7, 14, and 21, starting at 30 mins post treatment and/or 24 hours post treatment.

In addition, blood-plasma, dorsal root ganglia (DRG), and spinal cords are harvested from the treated animals in these studies in order to assay changes in the expression of inflammatory mediators. Such markers are measured at the gene expression level by RT-qPCR and in DRG and spinal cord tissue samples by immunohistochemistry.

Male Sprague-Dawley rats were treated with 2.4 mg/kg OXA (Sequoia Research Products, Pangbourne, UK) dissolved in a 5% glucose-water solution, administered i.p. for 5 consecutive days every week for 3 weeks (15 i.p. injections). RgIA or CSP-4 were injected i.m. alternatively into the right and left vastus lateralis muscle beginning on the first day of OXA administration, at three dose levels: 0.89 nmol/kg, 2.67 nmol/kg, and 8.0 nmol/kg. Measurements were performed on days 0, 7, 14, and 21 starting at 30 minutes post treatment and/or 24 hours post treatment as indicated in FIG. 4. Mechanical hyperalgesia was measured by the Randall-Selitto test. Mechanical allodynia was measured as described herein using the von Frey test. Cold-allodynia was measured using a cold plate test, wherein the cold plate was held at 4° C. and the time until the first sign of pain-related behavior (including lifting and/or licking of the paw in contact with the cold plate) was measured.

Mechanical hyperalgesia. RgIA and CSP-4 significantly prevented OXA-induced hyperalgesia at all three doses tested (0.89, 2.67, and 8.0 nmol $kg^{-1}$) (FIG. 4A-D). RgIA and CSP-4 acutely increased pain threshold when measured 30 min after injection. Efficacy was still significant at 24 h after. Pregabalin showed a similar profile to conotoxin peptides dosed at 0.89 nmol $kg^{-1}$ (the lowest dose tested).

Mechanical allodynia. Von Frey test measurements for mechanical allodynia are reported in shown in FIGS. 4E-H.

On day 7, pain threshold decreases induced by OXA treatment were reverted 30 min after the administration of 2.67 and 8.0 nmol kg$^{-1}$ of RgIA and CSP-4; 24 h later the analgesic effect was not observed. Pregabalin showed a similar effect. On days 14 and 21 RgIA and CSP-4 (all dosages) and pregabalin were active both at both 30 min and 24 h after injection, demonstrating a long lasting analgesic effect for RgIA and CSP-4.

Figure 4A:
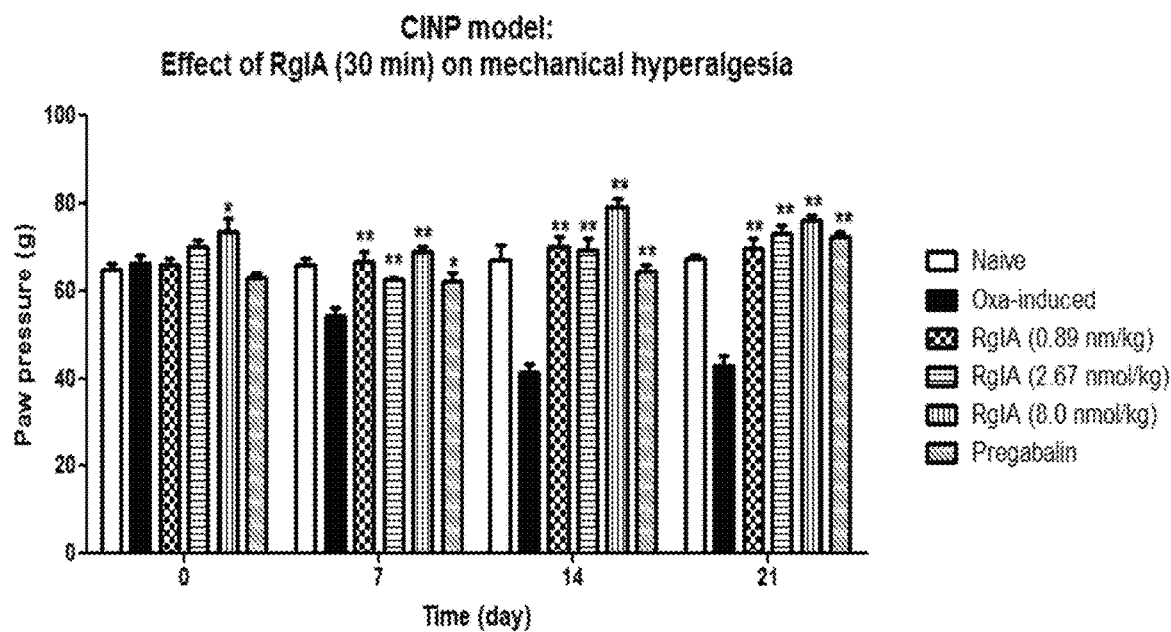
Figure 4B:
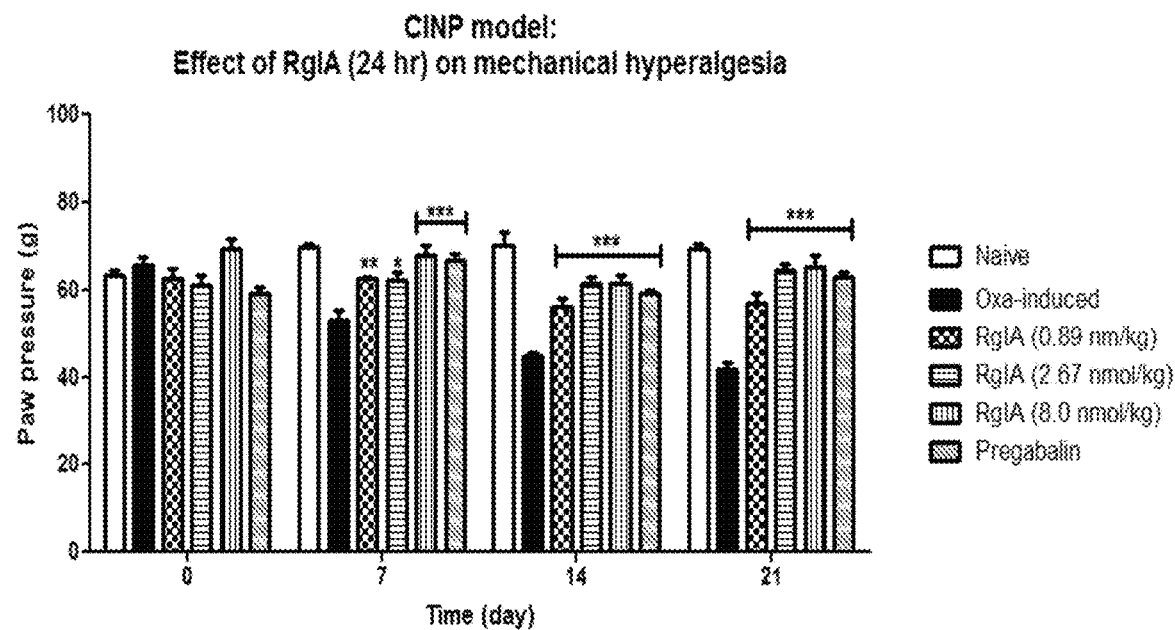
Figure 4C:
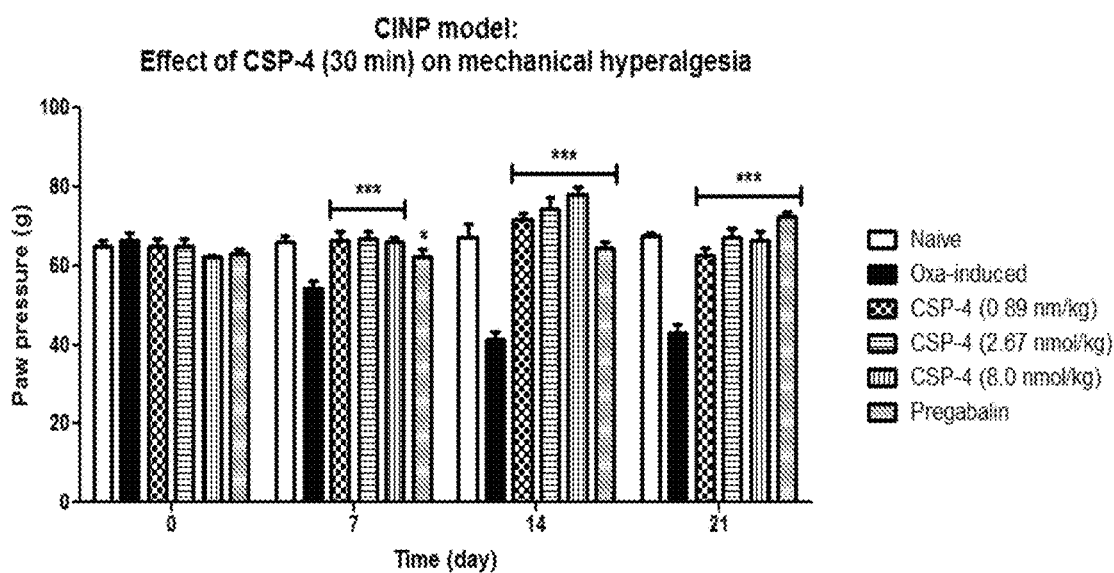
Figure 4D:
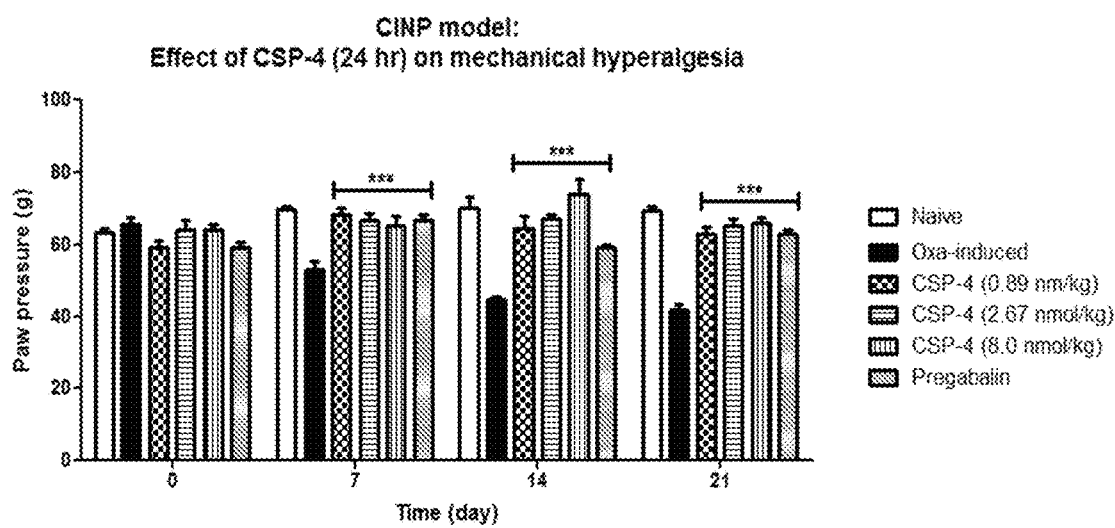
Figure 4E:
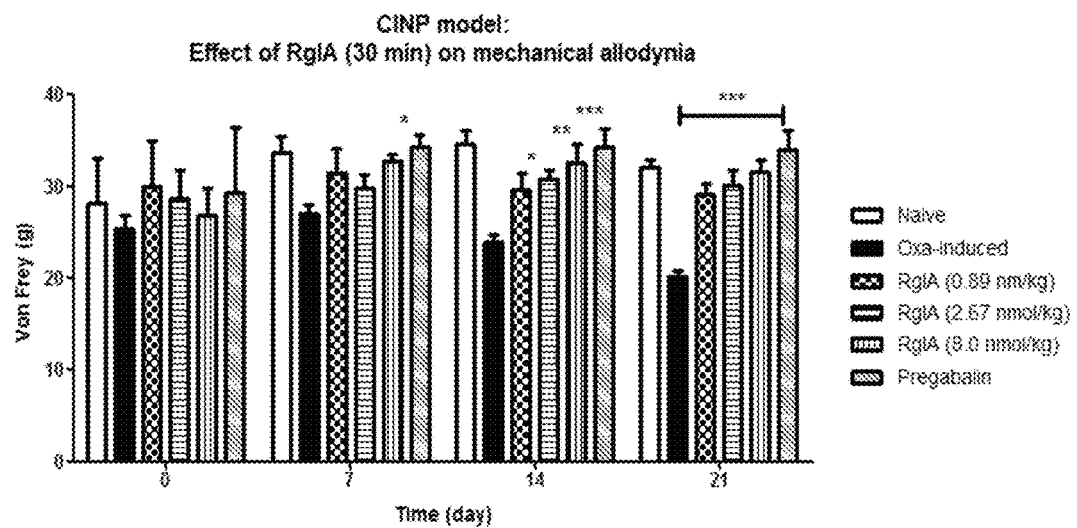
Figure 4F:
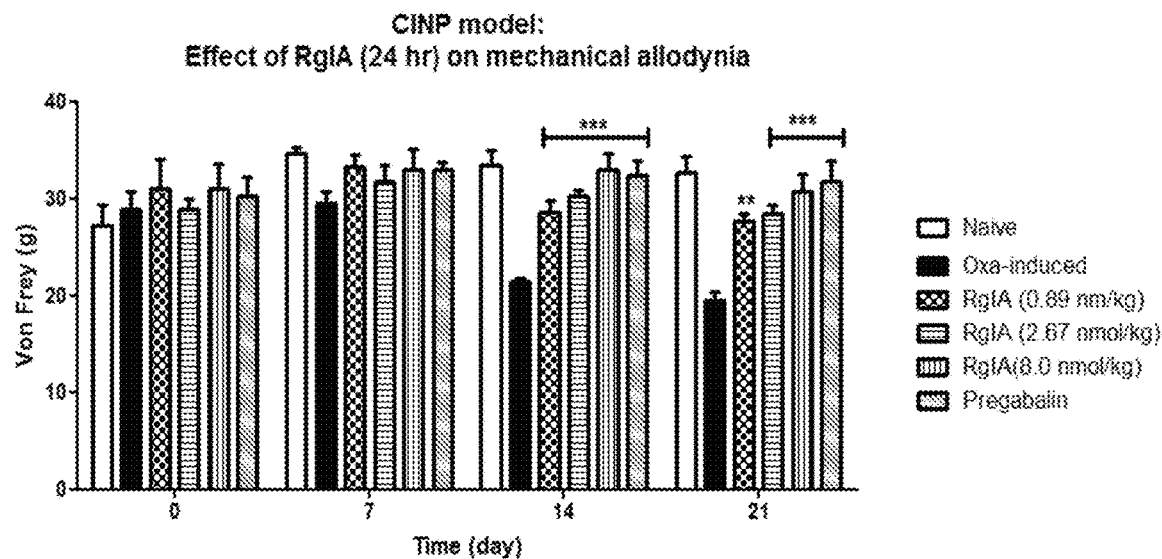
Figure 4G:
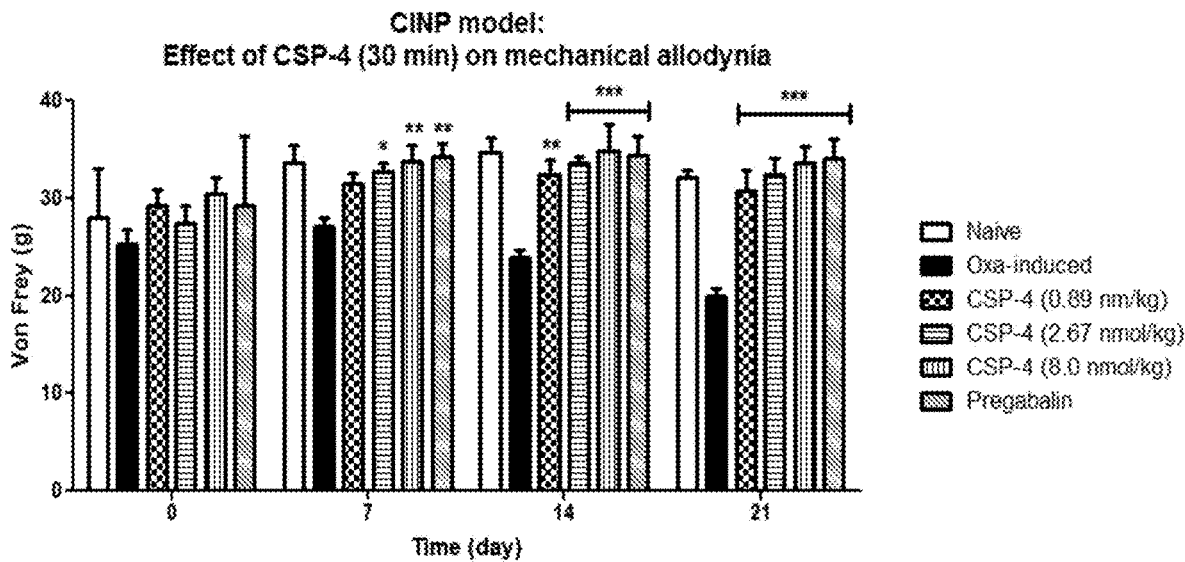
Figure 4H:
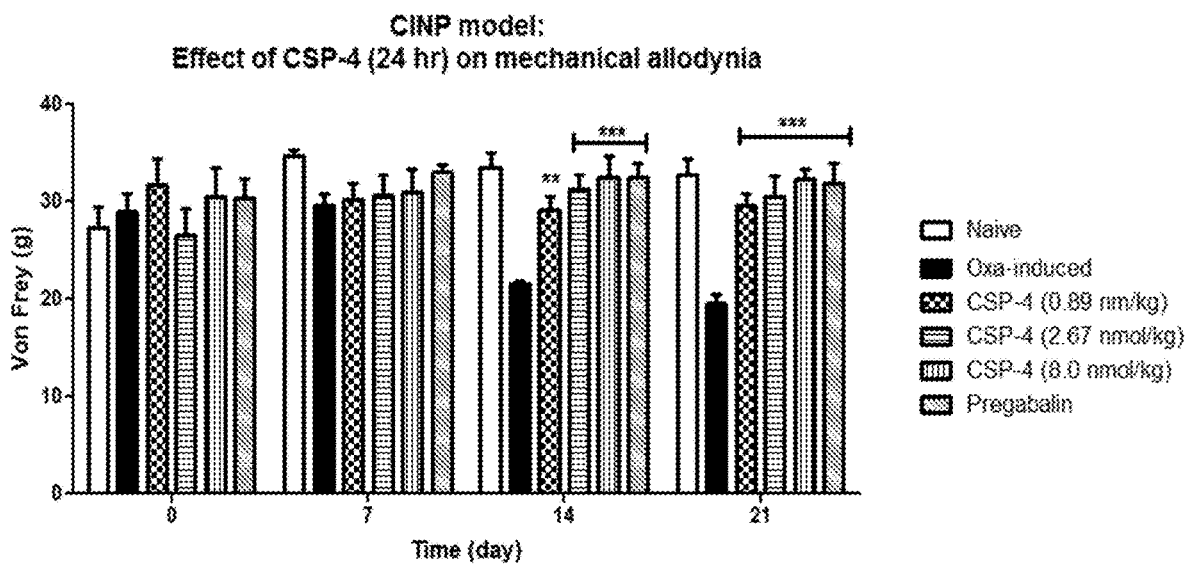
Figure 4I:
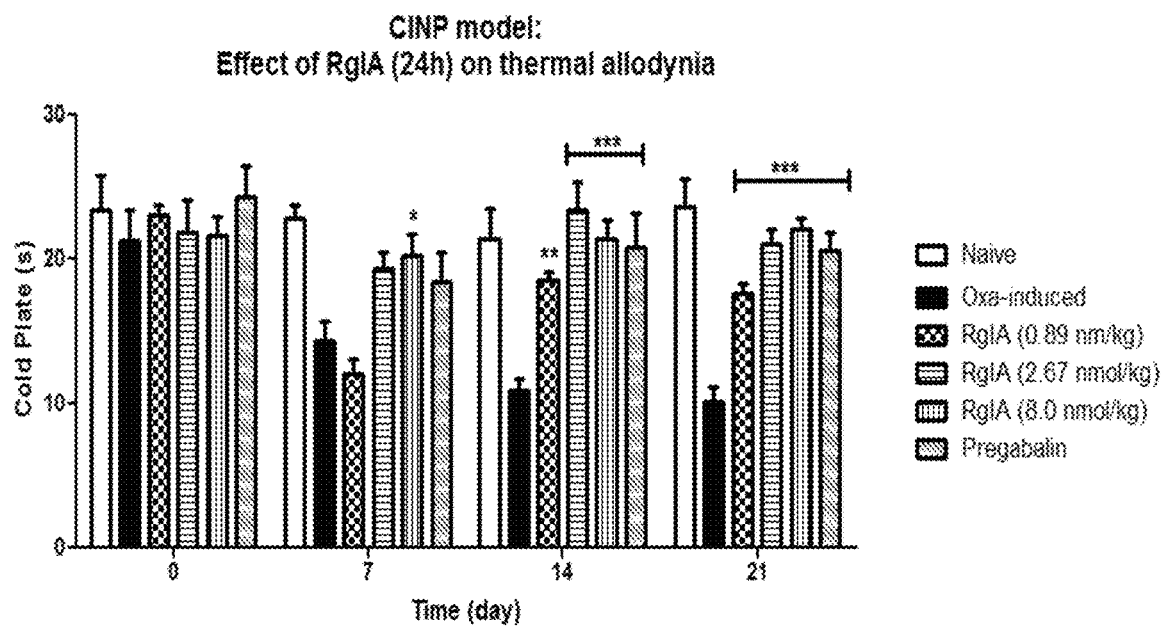
Figure 4J:
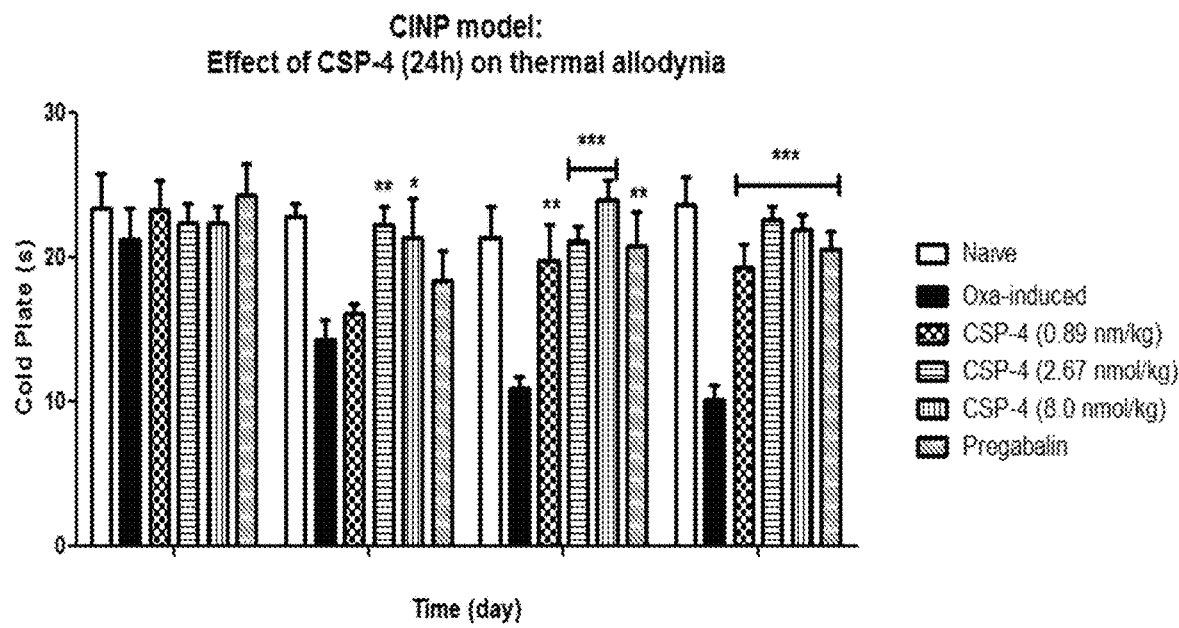

Thermal allodynia. Thermal allodynia was evaluated by the cold plate test and the results are shown in FIGS. 4I, and 4J. Repeated administration of RgIA and CSP-4 (2.67 and 8.0 nmol kg$^{-1}$ on day 7, and all dosages on day 14 and 21) were able to prevent OXA-induced cold allodynia.

Example 6. Efficacy in Full Thickness Injury (Burn) Pain Model

Burn injury involves both neuropathic and inflammatory components. An in vivo model of burn injury in the rat, such as the model described in Example 4 (full thickness thermal injury model; FTTI), has shown burn-induced mechanical allodynia and thermal hyperalgesia.

It has been shown that acute treatment with RgIA effectively reduces both thermal hyperalgesia and mechanical allodynia in the FTTI model. Conotoxin peptides that have shown greater potency on the human α9α10 nAChR channel as compared to RgIA are evaluated for their ability to reduce burn-induced pain as measured by reduction in one or more of the following: mechanical allodynia, thermal hyperalgesia, and/or expression of inflammatory markers.

Rats with unilateral hind paw FTTI receive a single injection per day of conotoxin peptide for 14 days, or an equivalently dosed negative control saline injection. To study the dose-dependent effects, at least three doses of the conotoxin peptides are tested. Injection of drug can be administered by routes including s.c. or i.m.

The antinociceptive effects of the analogs are measured over a time course of days 1, 4, 7, and 14 post-injury/post-treatment. As described previously, mechanical allodynia is measured by the von Frey method and thermal hyperalgesia is measured by the Hargreaves method. In addition, levels of inflammatory markers are measured in blood-plasma, paw tissues, DRG, and spinal cord samples from the same animals. Inflammatory mediators that are measured by qPCR include Substance P, CGRP, TGF-β, TNF-α, IL-6, and IL-1β. Selective markers in the DRG and spinal cord are analyzed by immunohistochemistry using macrophage marker specific and T cell marker specific antibodies.

Figure 5A:
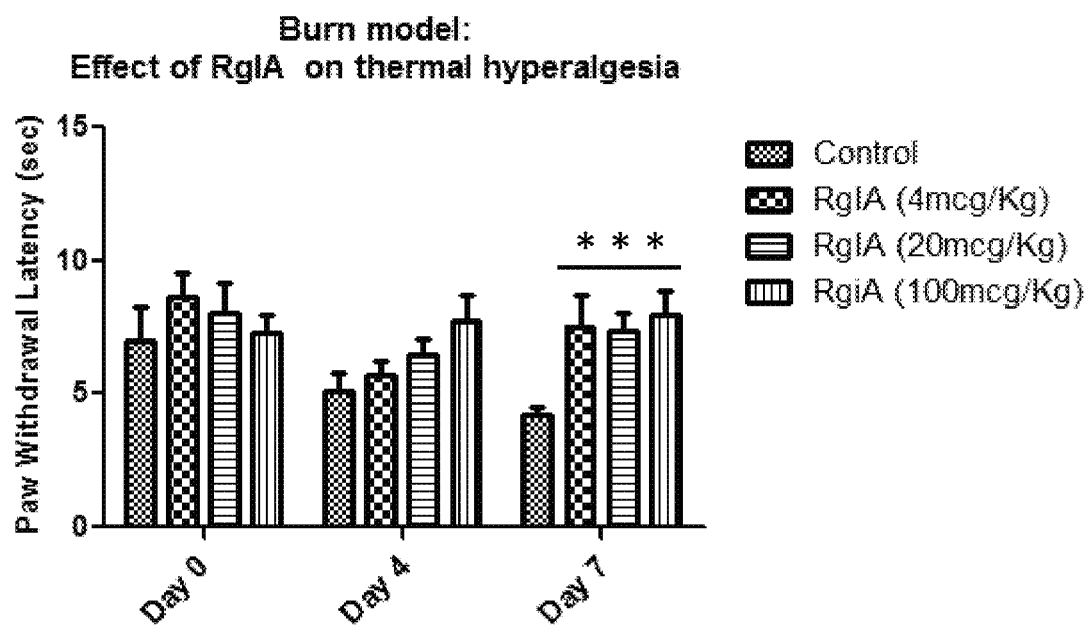
Figure 5B:
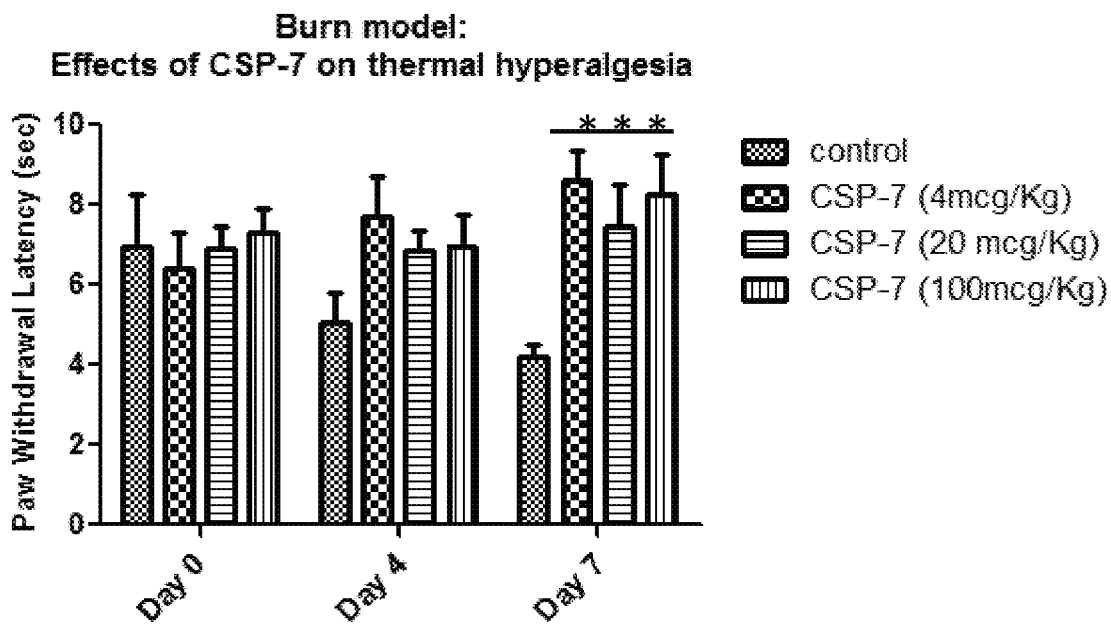

Data from one such study performed is shown in FIGS. 5A and 5B. RgIA (FIG. 5A) and Analog 11 (also referred to as CSP-7; SEQ ID NO:11) (FIG. 5B) significantly reduced burn-induced thermal hyperalgesia as measured by the Hargraves method at all three doses tested (4, 20, and 100 mcg/Kg).

Statistical analysis. Results were expressed as means □S.E.M. and the analysis of variance was performed by ANOVA. A Dunnet's significant difference procedure was used as post-hoc comparison. P values of less than 0.05 or 0.01 were considered significant.

Example 7. Efficacy in Post-Operative Neuropathic Pain Model

The paw incision model of post-surgical pain is designed to mimic pain that is experienced after surgery. The model involves making a 1 cm incision on the plantar surface of one paw in order to produce pain and sensitivity similar to what is reported by patients. Pre-surgery, measurements of mechanical sensitivity and mechanical hyperalgesia are taken as described below, in order to provide baseline values for assessment of conotoxin peptide efficacy at reducing mechanical allodynia and hyperalgesia.

Rats receive a single injection per day of a conotoxin peptide for 7 days, or an equivalently dosed negative control saline injection or positive control morphine injection. The dose-dependent effects of the conotoxin peptides can be tested by dosing at multiple dose levels. Injections can be administered by routes including s.c. or i.m.

Mechanical allodynia is measured by the von Frey method. Measurements are taken pre-surgery (days −3 and 0), approximately 2 hrs post-surgery (day 0), and on days 1, 2, 4, and 7 post-surgery approximately 30 minutes post-dosing with conotoxin peptide. Values for mechanical sensitivity are measured using an electronic von Frey device (eVF, IITC Life Sciences©; Woodland Hills, Calif.). Animals are placed in individual acrylic chambers on a metal mesh surface and allowed to acclimate to their surroundings for a minimum of 15 minutes before testing. The stimulus is presented perpendicular to the plantar surface of the paw and pressure is applied gradually. Paw withdrawal threshold values are recorded when a positive response is noted (paw sharply withdrawn) or the paw is lifted off the mesh surface. Three eVF thresholds are measured for each hind paw per time point. The mean of the 3 values is taken as the paw withdrawal threshold for that time point. The stimulus is designed to measure a response threshold, is escapable, and causes no damage to the animal.

Mechanical hyperalgesia is measured by the digital Randall-Selitto paw pressure test. Measurements are taken pre-surgery (day −3) and on days 1, 2, 4, and 7 post-surgery approximately 2 hrs post-dosing. Animals are allowed to acclimate to the testing room for a minimum of 15 minutes before testing. Animals are placed in a restraint sling that suspends the animal, leaving the hind limbs available for testing. The stimulus is applied to the plantar surface of the hind paw by a cone-shaped tip and pressure is applied gradually over approximately 10 seconds. Paw compression threshold values are recorded at the first observed nocifensive behavior (vocalization, struggle, or withdrawal). One reading per paw is taken and a maximum stimulus cutoff of 300 grams is used to prevent injury to the animal. The stimulus is designed to measure a response threshold, is escapable, and causes no damage to the animal.

The practice of the present disclosure employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., Molecular Cloning (Cold Spring Harbor Laboratory Press, Cold Spring Harbor, N.Y., 1982); Sambrook et al., Molecular Cloning, 2nd Ed. (Cold Spring Harbor Laboratory Press, Cold Spring Harbor, N.Y., 1989); Sambrook and Russell, Molecular Cloning, 3rd Ed. (Cold Spring Harbor Laboratory Press, Cold Spring Harbor, N.Y., 2001); Ausubel et al., Current Protocols in Molecular Biology (John Wiley & Sons, updated through 2005); Glover, DNA Cloning (IRL Press, Oxford, 1985); Anand, Techniques for the Analysis of Complex Genomes, (Academic Press, New York, 1992); Guthrie and Fink, Guide to Yeast Genetics and Molecular Biology (Academic Press, New York, 1991); Harlow and Lane, Antibodies, (Cold Spring Harbor Laboratory Press, Cold Spring Harbor, N.Y., 1998); Jakoby and Pastan, 1979; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Riott, Essential Immunology, 6th Edition, (Blackwell Scientific Publications, Oxford, 1988); Hogan et al., Manipulating the Mouse Embryo, (Cold Spring Harbor Laboratory Press, Cold Spring Harbor, N.Y., 1986); Westerfield, M., The zebrafish book. A guide for the laboratory use of zebrafish (*Danio rerio*), 4th Ed., (Univ. of Oregon Press, Eugene, Oreg., 2000).

As will be understood by one of ordinary skill in the art, each embodiment disclosed herein can comprise, consist essentially of, or consist of its particular stated element, step, ingredient, or component. Thus, the terms "include" or "including" should be interpreted to recite: "comprise, consist of, or consist essentially of." As used herein, the transition term "comprise" or "comprises" means includes, but is not limited to, and allows for the inclusion of unspecified elements, steps, ingredients, or components, even in major amounts. The transitional phrase "consisting of" excludes any element, step, ingredient, or component not specified. The transition phrase "consisting essentially of" limits the scope of the embodiment to the specified elements, steps, ingredients, or components and to those that do not materially affect the embodiment. As used herein, a material effect would cause a statistically significant reduction in the ability of a conotoxin peptide disclosed herein to block the α9/α10 subtype of the nAChR as compared to RgIA.

Unless otherwise indicated, all numbers used in the specification and claims are to be understood as being modified in all instances by the term “about.” Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term “about” has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms “a,” “an,” “the” and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., “such as”) provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to publications, patents, and/or patent applications (collectively “references”) throughout this specification. Each of the cited references is individually incorporated herein by reference for their particular cited teachings.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

REFERENCES

Abdrakhmonova et al. (2010). Neuropharm 59:511-517.
Arias et al. (2000). Int. J. Biochem. Cell. Biol. 32:1017-1028.
Armishaw et al. (2005). Curr. Protein Pept. Sci. 6:221-240.
Arredondo et al. (2002). J. Cell Biol. 159:325-336.
Authier, N., et al., Animal models of chemotherapy-evoked painful peripheral neuropathies. Neurotherapeutics, 2009. 6(4): p. 620-629.
Azam et al. (2012). J. Neurochem. 122:1137-1144.
Barreto-Chang et al. (2009). J. Vis. Exp. (23):1067.
Bennett et al. (1988). Pain 33:87-107.
Bennett et al. (1998). Biotechniques 24:478-482.
Bennett et al., (2003). Curr. Protoc. Pharmacol., 2003. Chapter 5: p. Unit 5 32.
Bodansky et al. (1966). Chem. Ind. 38:1597-1598.
Capelli et al. (2011). Br. J. Pharmacol. 163:313-329.
Chaplan et al. (1994). J. Neurosci. Methods 53(1):55-63.
Chen et al. (2011). Breast Cancer Res. Treat. 125:73-87.
Clark et al. Cyclised Alpha-conotoxin peptides, T.U.o. Queensland, Editor. 2013: AU.
Clark et al., (2012). Toxicon 59(4):446-55.
Craik et al. (2001). Toxicon 39:43-60.
Di Cesare et al. (2012). J. Pain, 13(3): 276-284.
Dutton et al. (2001). Curr. Med. Chem. 8:327-344.
Elgoyhen et al. (1994). Cell 79:705-715.
Elgoyhen et al. (2001). Proc. Natl. Acad. Sci. USA 98:3501-3506.
Ellison et al. (2006). Biochemistry 45:1511-1517.
Ettinger et al. (1978). Cancer 41:1270-1273.
Gerzanich et al. (1994). Mol. Pharmacol. 45:212-220.
Gotti et al. (2004). Prog. Neurobiol. 74:363-396.
Haberberger et al. (2004). Auton. Neurosci. 113:32-42.
Hargreaves et al. (1988). Pain 32:77-88.
Horiki, K. et al. (1978). Chemistry Letters 165-68.
Janes (2005). Curr. Opin. Pharmacol. 5:280-292.
Kaiser et al, (1970) Analytical Biochemistry 34 595
Kapoor (1970). J. Pharm. Sci. 59:1-27.
Karlin (2002). Nat. Rev. Neurosci. 3:102-114.
Kim et al. (1992). Pain 50:355-363.
Kracun et al. (2008). Br. J. Pharmacol. 153:1474-1484.
Kurzen et al. (2004). J. Invest. Dermatol. 123:937-949.
Le Novere et al. (2002). J. Neurobiol. 53:447-456.
Lee et al. (2010a). J. Natl. Cancer Inst. 102:1322-1335.
Lee et al. (2010b). Breast Cancer Res. Treat. 2010 Oct. 16. [Epub ahead of print].
Lewis (2004). IUBMB Life 56:89-93.
Linnoila (2010). J. Natl. Cancer Inst. 102:1298-1299.
Lips et al. (2002). Neuroscience 115:1-5.
Livett et al. (2004). Curr. Med. Chem. 11:1715-1723.
Luer et al. (1993). Annals Pharmcotherapy 27:912-921.
*Methoden der Organischen Chemie (Houben-Weyl): Synthese von Peptiden*, E. Wunsch (Ed.), Georg Thieme Verlag, Stuttgart, Ger. (1974).
McIntosh et al. (1999). Annu. Rev. Biochem. 68:59-88.
McIntosh et al. (2005). J. Biol. Chem. 280:30107-30112.
The Merck Manual of Diagnosis and Therapy, 17th Ed. (Merck & Co., Rahway, N.J., 1999).
Nguyen et al. (2000). Am. J. Pathol. 157:1377-1391.
Peng et al. (2004). Life Sci. 76:263-280.
Pitcher et al. (1999). J. Neurosci. Methods 87:185-193.
Remington: The Science and Practice of Pharmacy, 21st Ed., Lippincott Williams & Wilkins, Philadelphia, 2005.
Rivier, J. R. et al. (1978). Biopolymers 17:1927-1938.
Schroder & Lubke (1965). The Peptides 1:72-75, Academic Press, NY.
Sgard et al. (2002). Mol. Pharmacol. 61:150-159.
Stewart and Young, (1969). Solid-Phase Peptide Synthesis, Freeman & Co., San Francisco, Calif.
Teichert et al. (2012). Proc. Natl. Acad. Sci. USA 109:1388-1395.
Terlau et al. (2004). Physiol. Rev. 84:41-68.
Vincler et al. (2006). Proc. Natl. Acad. Sci. USA 103:17880-17884.
Wang et al. (2004). Acta Biochim. Biophys. Sin 36:713-723.
Xiao et al. (2009). J. Neurosci. 29:12428-12439.
Xiao et al. (1998). Mol. Pharmacol. 54:322-333.
Zimm et al. (1984). Cancer Res. 44:1698-1701.

What is claimed is:

1. A conotoxin peptide comprising the formula of any one of SEQ ID NO: 30, SEQ ID NO: 31, SEQ ID NO: 32, SEQ ID NO: 33, SEQ ID NO: 34, or SEQ ID NO: 37.

2. The conotoxin peptide of claim 1, comprising the formula of any one of SEQ ID NO: 23, SEQ ID NO: 24, SEQ ID NO: 25, SEQ ID NO: 26, or SEQ ID NO: 29.

3. The conotoxin peptide of claim 1, comprising the formula of SEQ ID NO: 3, SEQ ID NO: 5, SEQ ID NO: 7, SEQ ID NO: 8, SEQ ID NO: 9, SEQ ID NO: 10, SEQ ID NO: 11, SEQ ID NO: 13, SEQ ID NO: 15, SEQ ID NO: 16, SEQ ID NO: 17, or SEQ ID NO: 18.

4. The conotoxin peptide of claim 1, wherein a Tyr, an iodo-Tyr, or a fluorescent tag is attached to the carboxylic acid group.

5. The conotoxin peptide of claim 1, wherein a Tyr, an iodo-Tyr, a pyroglutamate, or a fluorescent tag is attached to the N-terminus of the conotoxin peptide.

6. The conotoxin peptide of claim 1, further comprising an amide cyclized backbone.

7. A pharmaceutical composition comprising a conotoxin peptide comprising the formula of SEQ ID NO: 3, SEQ ID NO: 5, SEQ ID NO: 7, SEQ ID NO: 8, SEQ ID NO: 9, SEQ ID NO: 10, SEQ ID NO: 11, SEQ ID NO: 13, SEQ ID NO: 15, SEQ ID NO: 16, SEQ ID NO: 17, SEQ ID NO: 18, SEQ ID NO: 23, SEQ ID NO: 24, SEQ ID NO: 25, SEQ ID NO: 26, SEQ ID NO: 29, SEQ ID NO: 30, SEQ ID NO: 31, SEQ ID NO: 32, SEQ ID NO: 33, SEQ ID NO: 34, or SEQ ID NO: 37 or a salt thereof, and a pharmaceutically acceptable carrier.

8. A method for treating at least one condition associated with an α9α10 subtype of a nicotinic acetylcholine receptor (nAChR) in a subject in need thereof comprising administering to the subject a therapeutically effective amount of a pharmaceutical composition comprising a conotoxin peptide comprising the formula of SEQ ID NO: 3, SEQ ID NO: 5, SEQ ID NO: 7, SEQ ID NO: 8, SEQ ID NO: 9, SEQ ID NO: 10, SEQ ID NO: 11, SEQ ID NO: 13, SEQ ID NO: 15, SEQ ID NO: 16, SEQ ID NO: 17, SEQ ID NO: 18, SEQ ID NO: 23, SEQ ID NO: 24, SEQ ID NO: 25, SEQ ID NO: 26, SEQ ID NO: 29, SEQ ID NO: 30, SEQ ID NO: 31, SEQ ID NO: 32, SEQ ID NO: 33, SEQ ID NO: 34, or SEQ ID NO: 37, or a salt thereof, thereby treating the condition.

9. The method of claim 8, wherein the at least one condition is pain.

10. The method of claim 9, wherein the pain is general pain, chronic pain, neuropathic pain, nociceptive pain, inflammatory pain, pain induced by peripheral nerve damage, pain induced by an inflammatory disorder, pain induced by a metabolic disorder, pain induced by cancer, pain induced by chemotherapy, pain induced by a surgical procedure, or pain induced by a burn.

11. The method of claim 9, wherein the pain is chemotherapy-related chronic pain or chemotherapy-related neuropathy.

12. The method of claim 8, wherein the at least one condition is an inflammatory condition.

13. The method of claim 12, wherein the inflammatory condition is inflammation, chronic inflammation, a rheumatic disease, sepsis, fibromyalgia, inflammatory bowel disease, sarcoidosis, endometriosis, uterine fibroids, an inflammatory skin disease, an inflammatory condition of a lung, a disease associated with nervous system inflammation, periodontal disease, or cardiovascular disease.

14. The method of claim 8, wherein the at least one condition is pain and inflammation.

15. The method of claim 8, wherein the at least one condition is inflammation and neuropathy.

16. The method of claim 8, wherein the at least one condition is mediated by immune cells.

17. The method of claim 8, wherein the at least one condition is long-term inflammation and peripheral neuropathy following injury.

18. The method of claim 8, wherein the at least one condition is breast cancer.

19. The method of claim 8, the pharmaceutical composition further comprising a pharmaceutically acceptable carrier.

* * * * *